US009697338B2

(12) United States Patent
Eiler et al.

(10) Patent No.: US 9,697,338 B2
(45) Date of Patent: Jul. 4, 2017

(54) HIGH-RESOLUTION MASS SPECTROMETER AND METHODS FOR DETERMINING THE ISOTOPIC ANATOMY OF ORGANIC AND VOLATILE MOLECULES

(71) Applicants: California Institute of Technology, Pasadena, CA (US); Thermo Fisher Scientific (Bremen) GmbH, Bremen (DE)

(72) Inventors: John M. Eiler, Pasadena, CA (US); Johannes Schwieters, Ganderkesee (DE)

(73) Assignees: CALIFORNIA INSTITUTE OF TECHNOLOGY, Pasadena, CA (US); THERMO FISHER SCIENTIFIC (BREMEN) GMBH (DE)

( * ) Notice: Subject to any disclaimer, the term of this patent is extended or adjusted under 35 U.S.C. 154(b) by 891 days.

(21) Appl. No.: 13/656,447

(22) Filed: Oct. 19, 2012

(65) Prior Publication Data
US 2013/0103337 A1     Apr. 25, 2013

Related U.S. Application Data

(60) Provisional application No. 61/550,272, filed on Oct. 21, 2011, provisional application No. 61/652,095, filed on May 25, 2012.

(51) Int. Cl.
*H01J 49/26* (2006.01)
*G06F 19/00* (2011.01)

(52) U.S. Cl.
CPC .................................. *G06F 19/703* (2013.01)

(58) Field of Classification Search
USPC .......................................................... 702/86
See application file for complete search history.

(56) References Cited

U.S. PATENT DOCUMENTS 3,849,656 A   11/1974  Wallington
5,194,732 A    3/1993  Bateman
(Continued)

FOREIGN PATENT DOCUMENTS

EP     1339089 A1    8/2003
EP     2128791 A2   12/2009
(Continued)

OTHER PUBLICATIONS

Peter M. van Galen, Research Assistant Mass Spectrometry, Organic Chemistry Department, Nijmegen University, Sep. 2005, 47 pages.*

(Continued)

*Primary Examiner* — Tung Lau
(74) *Attorney, Agent, or Firm* — Lewis Roca Rothgerber Christie LLP

(57) ABSTRACT

A mass spectrometer including an entrance slit, an energy filter, a momentum filter and a detector array, the entrance slit, energy filter and momentum filter being configured to provide molecular analyte ions to the detector array at a mass resolution of about 20,000 or greater. A method for determining the isotopic composition of an analyte in a sample includes converting the analyte to molecular analyte ions, separating the molecular analyte ions using an entrance slit, separating the molecular analyte ions according to their energy levels, separating the molecular analyte ions according to their momenta, detecting two or more of the molecular analyte ions at a mass resolution of about 20,000 or greater to produce molecular analyte ion data; and analyzing the molecular analyte data to determine the isotopic composition of at least a portion of the analyte.

18 Claims, 19 Drawing Sheets

(56) References Cited

U.S. PATENT DOCUMENTS

| | | | |
|---|---|---|---|
| 5,347,125 | A | 9/1994 | Holmes et al. |
| 5,723,862 | A | 3/1998 | Forman |
| 6,297,501 | B1 | 10/2001 | Merren |
| 7,653,494 | B2 | 1/2010 | Neascu et al. |
| 7,979,258 | B2 | 7/2011 | Goldberg et al. |
| 8,895,915 | B2* | 11/2014 | Schwieters ............ H01J 49/025 250/281 |
| 2002/0102610 | A1* | 8/2002 | Townsend .......... G01N 33/6818 435/7.1 |
| 2004/0004616 | A1 | 1/2004 | Konya et al. |
| 2004/0046116 | A1 | 3/2004 | Schroeder et al. |
| 2004/0083063 | A1 | 4/2004 | McClure |
| 2005/0086017 | A1 | 4/2005 | Wang |
| 2005/0255606 | A1 | 11/2005 | Ahmed et al. |
| 2006/0228301 | A1 | 10/2006 | Boros |
| 2007/0034810 | A1* | 2/2007 | Hoyes ................... H01J 49/427 250/396 R |
| 2010/0108879 | A1 | 5/2010 | Bateman et al. |
| 2011/0100222 | A1 | 5/2011 | Reilly |
| 2013/0124108 | A1 | 5/2013 | Eiler |
| 2014/0097338 | A1* | 4/2014 | Eiler ................... H01J 49/0009 250/282 |

FOREIGN PATENT DOCUMENTS

| | | |
|---|---|---|
| WO | WO 94/07257 | 3/1994 |
| WO | WO 2011/128702 A1 | 10/2011 |
| WO | WO 2013/070304 | 5/2013 |

OTHER PUBLICATIONS

Stanislav S. Rubakhin and Jonathan V. Sweedler, A mass spectrometry primer for mass spectrometry imaging, 29 pages, Apr. 7, 2011.*

Mass Spectrometry: Quadrupole Mass Filter, Advanced Lab, Jan. 2008, 8 pages.*

International Search Report and Written Opinion of the International Searching Authority for PCT/US2012/061191, dated Mar. 29, 2013, 10 pages.

International Search Report and Written Opinion of the International Searching Authority for PCT/US2012/061192, dated Mar. 28, 2013, 11 pages.

International Search Report and Written Opinion of the International Searching Authority for PCT/US2013/064409, dated Jan. 16, 2014, 11 pages.

Baldwin, "Protein Identification by Mass Spectrometry", Molecular & Cellular Proteomics 3.1, 2004, The American Society for Biochemistry and Molecular Biology, Inc., pp. 1-9.

Palaniappan, "Istopic Signature Transfer and Mass Pattern Prediction (IsoStamp): An Enabling Technique for Chemically-Directed Proteomics." *ACS Chem. Biol.* 2011, 6, (pp. 829-836).

* cited by examiner ical compounds. More
HIGH-RESOLUTION MASS SPECTROMETER AND METHODS FOR DETERMINING THE ISOTOPIC ANATOMY OF ORGANIC AND VOLATILE MOLECULES

CROSS-REFERENCE TO RELATED APPLICATION(S)

This non-provisional application claims priority to and the benefit of U.S. Provisional Application Ser. No. 61/550,272, filed on Oct. 21, 2011, entitled HIGH-RESOLUTION MASS SPECTROMETER AND METHODS FOR DETERMINING THE ISOTOPIC ANATOMY OF ORGANIC AND VOLATILE COMPOUNDS, and U.S. Provisional Application Ser. No. 61/652,095, filed on May 25, 2012, entitled SYSTEM AND METHOD FOR DETERMINING THE ISOTOPIC ANATOMY OF ORGANIC AND VOLATILE MOLECULES, the entire contents of each of which are incorporated herein by reference.

STATEMENT REGARDING FEDERALLY SPONSORED RESEARCH OR DEVELOPMENT

This invention was made with government support under Award No. EAR0949336 awarded by the National Science Foundation. The government has certain rights in the invention.

FIELD

The following description generally relates to methods for determining the isotopic anatomy of an analyte, such as molecular gases and volatile organic compounds. More particularly, the following description relates to apparatus for measuring intensity ratios of molecular ions, fragment ions and adduct ions, and to methods for determining abundance ratios of isotopologues and position-specific isotopic compositions within a sample or samples.

BACKGROUND

Conventional mass spectrometry primarily focuses on measuring the concentrations of isotopic species including only one rare isotope. These mass spectrometric techniques generally determine the overall concentration of an isotope, irrespective of its location in the molecule (i.e., the atomic site or sites of isotopic substitution) or the proportions of multiple isotopic substitutions within the same molecule. Consequently, conventional mass spectrometry fails to distinguish among different isotopologues of the same molecule and thus disregards a large amount of useful information that can be determined from a complete analysis of all the different isotopologues present in a sample. However, determining the isotopic composition of a molecule including more than one rare isotope can provide useful information, such as the geographic origin of the molecule, temperature of origin of the molecule (or a sample including the molecule) or the identity of a parent molecule from which the molecule was derived.

The shortcomings of conventional mass spectrometry are particularly noteworthy for organic compounds, which may have large numbers of isotopologues. For example, methane ($CH_4$) has 57 distinct isotopic versions including various non-equivalent combinations of $^{12}C$, $^{13}C$, $^{14}C$, hydrogen, deuterium, and tritium. The number of isotopologues of low-symmetry molecular structures grows approximately geometrically with the number of atomic positions, meaning alkanes, lipids, sugars and other complex hydrocarbons containing several or more carbon atoms typically have at least several hundred distinct isotopologues; many such molecules have $10^6$ or more distinct isotopologues. Abundances of only a small subset of these species (typically 2-5) are meaningfully constrained by commonly recognized methods of isotopic analysis.

Although other methods have been developed to expand the set of isotopologues that can be analyzed with useful precision, these methods are applicable to a relatively narrow range of sample types and sizes and to a restricted range of isotopic species in a given analyte target. For example, demonstrated site-specific natural isotope fractionation-nuclear magnetic resonance (SNIF-NMR) techniques can determine, for example, relative deuterium concentration and specific deuterium-site locations in a molecule based on the deuterium NMR signal obtained for the molecule. Comparison of the relative deuterium concentration of the molecule with known global distributions of hydrogen isotope concentrations can provide information regarding the geographic origin of a sample from which the molecule was obtained. SNIF-NMR techniques, however, are not capable of analyzing abundances of molecules containing two or more rare isotopes at their natural abundances and, more generally, require sample sizes that are prohibitively large for many applications and require relatively long, costly analyses. Similarly, established "clumped isotope" mass spectrometric methods can analyze only a few isotopologues of small, simple, highly volatile molecules, principally because of their inability to resolve isobaric interferences and the poor sensitivity of existing gas source multi-collector sector mass spectrometers. Clumped isotope geochemistry and related techniques are described in more detail in "'Clumped-isotope' geochemistry—The study of naturally-occurring, multiply-substituted isotopologues," Earth and Planetary Science Letters, Vol. 262, Issues 3-4, pages 309-327, the entire contents of which are herein incorporated by reference.

SUMMARY

Aspects of embodiments of the invention are directed to apparatus and methods for the quantitative analysis of the isotopologues of gaseous compounds and/or volatile organic compounds. According to one embodiment, the gaseous compounds and/or volatile organic compounds are introduced into a gas source isotope ratio mass spectrometer, which converts the compounds into molecular ion, fragment ion and/or adduct ion beams, which are analyzed to determine the isotopic composition of the gaseous compounds and/or volatile organic compounds. Aspects of embodiments are also directed to methods of data processing and standardization for converting measured intensity ratios of isotopic species into abundance ratios of isotopologues, including multiply-substituted isotopologues and position-specific isotopic compositions.

Embodiments of the invention are also directed to various applications of the apparatus and methods, such as applications in earth and environmental science (e.g., thermometry of natural compounds and developing budgets for atmospheric gases), chemistry, forensics (e.g., chemical forensics and explosives fingerprinting), biomedical research, diagnosis and treatment of diseases (e.g., drug and/or drug metabolite tracking), and hydrocarbon (e.g., oil and gas) exploration. For example, embodiments of the invention are directed to identifying the location of oil and gas deposits (e.g., a potential oil-field) based on the relative proportion of isotopologues (e.g., isotopologues of methane) of a sample as determined using the apparatus and methods described herein.

For example, one embodiment of the invention is directed to the determination of relative abundances of the methane isotopologues: $^{12}CH_4$, $^{13}CH_4$, $^{12}CH_3D$ and $^{13}CH_3D$. The apparatus and methods described herein can be used to obtain molecular analyte ion data from a sample of methane. The molecular analyte ion data can then be used to determine the isotopic compositions of the constituent components of the sample and, thus, the relative abundances of the $^{12}CH_4$, $^{13}CH_4$, $^{12}CH_3D$ and $^{13}CH_3D$ isotopologues in the methane sample. The relative proportions of the preceding methane isotopologues are a function of temperature in methane that has achieved thermodynamic equilibrium. Thus, a determination of the relative proportions of the preceding isotopologues in a sample of methane can be used to measure the temperatures of origin and/or storage of this component of natural gas, as an aid to the exploration and development of oil and gas deposits.

Another embodiment is directed to the determination of relative abundances of $^{13}C$-bearing isotopologues of $CH_3^+$ and $C_2H_5^+$ ion fragments generated by ionization of propane. The foregoing data, combined with characterizations of the empirical constants describing fragmentation and recombination reactions in the ion source, can be used to determine the difference in $^{13}C$ content between the terminal and central carbon positions of propane. This difference is predicted to be a function of temperature in thermodynamically equilibrated propane (and thus can be used to establish the temperature of formation, as for the methane analysis described above). In non-equilibrated gases, this difference may illuminate the chemical kinetic mechanisms of natural gas maturation, and thus also aid in the exploration and development of oil and gas deposits.

Yet another embodiment of the invention is directed to the analysis of relative proportions of $^{13}C$, D and/or $^{18}O$ bearing isotopologues of ion fragments generated by delivering volatile organic compounds, such as derivatized sugars, into the ion source. The foregoing data, combined with characterizations of the empirical constants describing fragmentation and recombination reactions in the ion source, will allow for the characterization of isotopic fingerprints associated with diverse sources of such compounds and thus aid in the forensic studies of diverse organic compounds (functionally, any species that can be derivatized to create a compound that can be delivered to the ion source through a heated gas chromatographic column).

According to embodiments of the invention, a mass spectrometer includes an entrance slit having a width. The slit is configured to guide a first output of molecular analyte ions along a path, the molecular analyte ions of the first output having energy levels. An energy filter is positioned along the path downstream from the entrance slit and is configured to receive the first output of molecular analyte ions, the energy filter having a first radius of curvature along the path. The energy filter is configured to filter the molecular analyte ions of the first output according to their energy levels and produce a second output of molecular analyte ions. A momentum filter is positioned downstream from the energy filter and is configured to receive the second output of molecular analyte ions, the momentum filter having a second radius of curvature along the path. The momentum filter is configured to filter the molecular analyte ions of the second output according to their momenta and produce a third output of molecular analyte ions. The mass spectrometer also includes a detector array positioned downstream of the momentum filter and configured to receive the third output of molecular analyte ions. The width and the first and second radii of curvature are selected to provide a mass resolution at the detector array of about 20,000 or greater.

The third output of molecular analyte ions can include at least two molecular analyte ion beams, respective molecular analyte ions of the ion beams having respective masses that differ from one another by less than or equal to about 1 atomic mass units, and the width, the first and second radii of curvature, and detector array can be configured to resolve and concurrently detect the at least two molecular analyte ion beams at the detector array, and to distinguish between molecular analyte ions within each beam at one part in 20,000. In still another embodiment, the third output of molecular analyte ions includes at least two molecular analyte ions, where the respective masses of the at least two molecular analyte ions are the same when rounded to the nearest whole number, the width and the first and second radii of curvature are configured to resolve the at least two molecular analyte ions at the detector array, and the detector array is configured to concurrently detect the at least two molecular analyte ions.

In some embodiments, the width of the entrance slit can vary from about 5 μm to about 250 μm, for example, by way of a mechanical device that translates slits of variable width in and out of the path of the ion beam through the mass spectrometer analyzer. In some embodiments, the first radius of curvature of the energy filter is about 20 cm to about 25 cm, and the second radius of curvature of the momentum filter is about 20 cm to about 25 cm. For example, the width of the entrance slit can be about 5 μm, the first radius of curvature of the energy filter (e.g., an electrostatic analyzer) can be about 22 cm, and the second radius of curvature of the momentum filter (e.g., a magnetic sector) can be about 23 cm (where the width of the entrance slit, first radius of curvature of the energy filter, the second radius of curvature of the momentum filter are consistent with the accelerating potentials on the ion beam such that the ion beam achieves a double focusing condition at the detectors).

The mass spectrometer can further include an ion source along the path upstream from the entrance slit. The ion source is configured to provide an electron impact energy of about 5 eV to about 150 eV and to provide the first output of molecular analyte ions to the entrance slit. For example, the ion source can be configured to provide an electron impact energy of about 25 eV to about 150 eV. In another embodiment, the ion source is capable of providing an electron impact energy of less than 50 eV.

The detector array can include two or more detectors, and at least one of the detectors can be movable along a focal plane of the mass spectrometer. In some embodiments, the position of the at least one detector is computer-controlled. In some embodiments, at least one detector includes a first collector and a second collector. The first collector and the second collector can be selected by computer control (e.g., a computer can be used to switch between the first collector and the second collector). In some embodiments, the first collector is a current monitoring system and the second collector is an ion counting system.

Aspects of embodiments of the invention are also directed to applications of the mass spectrometer. For example, according to embodiments of the invention, a method of identifying a high-potential oil-field includes analyzing an analyte of a sample from a target field using an embodiment of the mass spectrometer described herein to obtain molecular analyte ion data. The method further includes analyzing the molecular analyte ion data to obtain the isotopic composition of at least a portion of the analyte. The isotopic composition of the analyte is used to determine relative proportions of at least a portion of isotopologues in the sample. The relative proportions of the isotopologues of the sample are compared to a database to determine a property of the sample, such as the temperature of origin (e.g., temperature of formation) and/or temperature of storage of the sample. The temperature of origin (e.g., temperature of formation) and/or temperature of storage of the sample can be used in conjunction with other information to decide whether or not to drill at the target field. In some embodiments, the analyte is a hydrocarbon, such as methane, ethane, propane, butane, pentane and hexane.

According to another embodiment of the invention, a method of analyzing a drug or drug metabolite includes analyzing the drug or drug metabolite in a sample using an embodiment of the mass spectrometer described herein to convert the drug or drug metabolite to molecular analyte ions and to obtain molecular analyte ion data. The method also includes analyzing the molecular analyte ion data to obtain the isotopic composition of at least a portion of the drug or drug metabolite. The method further includes comparing the isotopic composition obtained for the drug or drug metabolite to a database of isotopic compositions. The correlation between the isotopic composition obtained for the drug or drug metabolite and the database of isotopic compositions can be used to determine a property of the drug or the drug metabolite and is useful in the forensic study of diverse organic compounds.

According to embodiments of the invention, a method of determining an amount of an anthropogenic contribution to an atmospheric concentration of an atmospheric gas includes analyzing an analyte of a sample using an embodiment of the mass spectrometer described herein to obtain molecular analyte ion data. The method further includes analyzing the molecular analyte ion data to obtain the isotopic composition of at least a portion of the analyte. The method also includes comparing the isotopic composition obtained for the analyte to a database of isotopic compositions. The correlation between the isotopic composition obtained for the analyte and the database of the isotopic compositions can be used to determine the amount of the anthropogenic contribution to the atmospheric concentration of the atmospheric gas.

According to another embodiment of the invention, a method for the diagnosis or treatment of a disease includes analyzing an analyte of a sample from a patient using an embodiment of the mass spectrometer described herein to obtain molecular analyte ion data. The method further includes analyzing the molecular analyte ion data to obtain the isotopic composition of at least a portion of the analyte. The method also includes comparing the isotopic composition obtained for the analyte to a database of isotopic compositions. The correlation between the isotopic composition obtained for the analyte and the database of the isotopic compositions can be used to determine a disease diagnosis or disease treatment protocol.

According to another embodiment of the invention, a method for determining a prior temperature of a sample includes analyzing an analyte of the sample using an embodiment of the mass spectrometer described herein to obtain molecular analyte ion data. The method further includes analyzing the molecular analyte ion data to obtain the isotopic composition of at least a portion of the analyte. The method also includes comparing the isotopic composition obtained for the analyte to a database of isotopic compositions. The correlation between the isotopic composition obtained for the analyte and the database of isotopic compositions can be used to determine the prior temperature of the sample.

Aspects of embodiments of the invention are also directed to methods for determining the isotopic composition of an analyte in a sample. For example, according to embodiments of the invention, a method for determining the isotopic composition of an analyte in a sample includes converting the analyte to molecular analyte ions using an ion source in a mass spectrometer to produce a first output of the molecular analyte ions. The method further includes separating at least a portion of the first output of the molecular analyte ions using an entrance slit, further separating at least a portion of the molecular analyte ions of the first output according to their energy levels to produce a second output of molecular analyte ions, and separating at least a portion of the molecular analyte ions of the second output according to their momenta to produce a third output of molecular analyte ions. The method also includes detecting two or more molecular analyte ions of the third output at a mass resolution of about 20,000 or greater to produce molecular analyte ion data. The method further includes analyzing the molecular analyte ion data to determine the isotopic composition of at least a portion of the analyte.

The third output can include two or more molecular analyte ion beams and the detecting the two or more molecular analyte ions can include scanning at least one of the molecular analyte ion beams across at least one detector. Respective molecular analyte ions of the two or more molecular analyte ion beams can have masses that differ from one another by less than or equal to about 1 atomic mass unit. The scanning the at least one molecular analyte ion beam across the at least one detector produces a change in a detected signal intensity as masses of molecular analyte ions detected by the detector change at an amount of one part in 20,000. The method can further include introducing the analyte to the mass spectrometer as a continuous flow prior to converting the analyte to the analyte ions.

In some embodiments, the third output includes two or more molecular analyte ion beams and the detecting the two or more molecular analyte ions includes concurrently detecting at least two of the molecular analyte ion beams using separate detectors. Respective molecular analyte ions of the two or more molecular analyte ion beams can have masses that differ from one another by more than about 1 atomic mass unit. In some embodiments, the method further includes introducing the analyte to the mass spectrometer as a continuous flow prior to converting the analyte to the analyte ions. In other embodiments, the method includes introducing the sample to the mass spectrometer as a time-resolved pulse prior to converting the analyte to the analyte ions.

In some embodiments, the analyzing the molecular analyte ion data can include deconvolving the molecular analyte ion data to identify the relative contribution of each of the two or more molecular analyte ions to the molecular analyte ion data. The analyte can include two or more analyte isotopologues, analyte isotopomers or mixtures thereof. The analyzing the molecular analyte ion data can further include determining the molecular position of at least one isotope in at least one of the analyte isotopologues or the analyte isotopomers.

In some embodiments, the method further includes standardizing the mass discrimination of the mass spectrometer. For example, the method can further include obtaining mass discrimination reference data from a mass discrimination reference material including mass discrimination reference isotopologues or isotopomers A-MD and B-MD having respective mass discrimination reference concentrations [A-MD] and [B-MD]. The mass discrimination reference data includes mass discrimination reference ion intensities $I_{A-MD}$ and $I_{B-MD}$ corresponding to the respective mass discrimination reference isotopologues or isotopomers A-MD and B-MD. The method further includes determining the mass discrimination of the mass spectrometer by comparing a ratio of the mass discrimination reference ion intensities $I_{A-MD}$ and $I_{B-MD}$ to a ratio of the mass discrimination reference concentrations [A-MD] and [B-MD] using a constant of proportionality $\alpha_{IMF}$ according to the Equation: $I_{A-MD}/I_{B-MD}=([A-MD]/[B-MD])\alpha_{IMF}$. The method can also further include modifying the molecular analyte data using $\alpha_{IMF}$.

In some embodiments, the method further includes standardizing the linearity of the mass spectrometer. For example, the method can further include obtaining first linearity reference data from a first linearity reference material including first linearity reference isotopologues or isotopomers A-1 and B-1 at a first linearity reference concentration ratio $([A-1]/[B-1])_1$. The first linearity reference data includes a first linearity reference intensity ratio $(I_{A-1}/I_{B-1})_1$ corresponding to the first linearity reference isotopologues or isotopomers A-1 and B-1. The method can also further include obtaining second linearity reference data from a second linearity reference material including second linearity reference isotopologues or isotopomers A-2 and B-2 at a second linearity reference concentration ratio $([A-2]/[B-2])_2$. The second linearity reference data includes a second linearity reference intensity ratio $(I_{A-2}/I_{B-2})_2$ corresponding to the second linearity reference isotopologues or isotopomers A-2 and B-2. The method can include determining the linearity (L) of the mass spectrometer according to the Equation: $(I_{A-1}/I_{B-1})_1/(I_{A-2}/I_{B-2})_2=\{([A-1]/[B-1])_1/([A-2]/[B-2])_2\}L$. The method can also further include modifying the molecular analyte ion data using the linearity L.

In some embodiments, the method further includes standardizing a ratio of molecular analyte adduct ions to intact molecular analyte ions. For example, the molecular analyte ions can include intact molecular analyte ions and molecular analyte adduct ions. Each of the intact molecular analyte ions is formed by ionizing an intact molecule of the analyte, and each of the molecular analyte adduct ions is formed by combining one or more of the intact molecules of the analyte or the intact molecular analyte ions and a hydrogen atom or an other material. The other material is the same as or different from the intact analyte molecule or the intact molecular analyte ions. The molecular analyte ion data can include an intact molecular analyte ion intensity $I_{A-molecular}$ corresponding to one or more of the intact molecular analyte ions and a molecular analyte adduct ion intensity $I_{A'-adduct}$ corresponding to one or more of the molecular analyte adduct ions. The method can further include determining a ratio of the molecular analyte adduct ions to the intact molecular analyte ions by calculating a constant of proportionality $K_{adduct}$ according to the Equation: $I_{A'-adduct}/I_{A-molecular}=K_{adduct}$. The method can further include modifying the molecular analyte data using $K_{adduct}$.

In some embodiments, the method further includes standardizing a ratio of molecular analyte fragment ions to intact molecular analyte ions. For example, the molecular analyte ions can include intact molecular analyte ions and molecular analyte fragment ions. Each of the intact molecular analyte ions is formed by ionizing an intact molecule of the analyte, and each of the molecular analyte fragment ions is formed by dissociating one or more of the intact molecules of the analyte or the molecular analyte ions. The molecular analyte ion data can include an intact molecular analyte ion intensity $I_{A-molecular}$ corresponding to one or more of the intact molecular analyte ions, and a molecular analyte fragment ion intensity $I_{FA}$ corresponding to one or more of the molecular analyte fragment ions. The method can further include determining a ratio of the molecular analyte fragment ions to the intact molecular analyte ions by calculating a constant of proportionality $K_{fragment}$ according to the Equation: $I_{FA}/I_{A-molecular}=K_{fragment}$. The method can further include modifying the molecular analyte data using $K_{fragment}$.

In some embodiments the method further includes determining a rate of recombination or redistribution of ions, molecules and electrons in the mass spectrometer. For example, the method can further include obtaining first recombination reference data from a first recombination reference material including first recombination reference isotopologues or isotopomers A-1 and B-1 and having a preset first recombination reference ratio of the first recombination reference isotopologues or isotopomers A-1 to the first recombination reference isotopologues or isotopomers B-1. The method further includes determining a constant of proportionality $K_{eq}^1$ from the first recombination reference data. The method can also include obtaining second recombination reference data from a second recombination reference material including second recombination reference isotopologues or isotopomers A-2 and B-2 and having a preset second recombination reference ratio of the second recombination reference isotopologues or isotopomers A-2 to the second recombination reference isotopologues or isotopomers B-2. The method can also include determining a constant of proportionality $K_{eq}^2$ from the second recombination reference data. The method can also further include determining a rate of recombination of ions, molecules and electrons in the mass spectrometer according to the Equation: $(K_{eq}^1/K_{eq}^2)_{measured}/(K_{eq}^1/K_{eq}^2)_{known}=K_{redistribution}$. The method can further include modifying the molecular analyte ion data using $K_{redistribution}$.

In some embodiments, the method further includes determining a constant of migration (e.g., standardizing migration of atoms within the mass spectrometer). For example, the method can further include obtaining migration reference data from a migration reference material including isotopomers having an initial migration reference concentration ratio $([D]_1/[D]_2)_{initial}$. The method can further include determining a measured migration reference concentration ratio $([D]_1/[D]_2)_{measured}$ from the migration reference data. The method can also include determining a constant of migration $K_{migration}$ according to the Equation: $([D]_1/[D]_2)_{measured}/([D]_1/[D]_2)_{initial}=K_{migration}$. The method can further include modifying the molecular analyte data using $K_{migration}$.

According to another embodiment of the invention, a method for determining the isotopic composition of an analyte in a sample includes converting the analyte to molecular analyte ions using an ion source in a mass spectrometer to produce a first output of the molecular analyte ions. The method further includes separating at least a portion of the molecular analyte ions using an entrance slit, further separating at least a portion of the molecular analyte ions of the first output according to their energy levels to produce a second output of molecular analyte ions and separating at least a portion of the molecular analyte ions of the second output according to their momenta to produce a third output of molecular analyte ions. The method further includes obtaining molecular analyte ion data from the third output. The method also includes obtaining one or more of mass discrimination reference data, first and second linearity reference data, first and second recombination reference data, and/or migration reference data, and determining one or more of a linearity (L), a constant of proportionality $\alpha_{IMF}$, a constant of proportionality $K_{adduct}$, a constant of proportionality $K_{fragment}$, a constant of proportionality $K_{redistribution}$, and/or a constant of migration $K_{migration}$ from the first and second linearity reference data, the mass discrimination reference data, the first and second linearity reference data, the molecular analyte ion data, the molecular analyte ion data, the first and second recombination reference data, and the migration reference data, respectively. The method further includes modifying the molecular analyte ion data using one or more of the constant of proportionality $\alpha_{IMF}$, the linearity (L), the constant of proportionality $K_{adduct}$, the constant of proportionality $K_{fragment}$, the constant of proportionality $K_{redistribution}$, and/or the constant of migration $K_{migration}$. The method also includes analyzing the molecular analyte ion data to determine the isotopic composition of at least a portion of the analyte.

According to another embodiment of the invention, a method of identifying a high-potential oil-field includes determining the isotopic composition of at least a portion of an analyte in a sample according to one of the methods described herein. The method further includes using the isotopic composition of the analyte to determine relative proportions of at least a portion of isotopologues in the sample. The relative proportions of the isotopologues of the sample are compared to a database to determine a property of the sample, such as the temperature of origin (e.g., temperature of formation) and/or temperature of storage of the sample. The temperature of origin (e.g., temperature of formation) and/or temperature of storage of the sample can be used in conjunction with other information to decide whether or not to drill at the target field. In some embodiments, the analyte is a hydrocarbon, such as methane, ethane, propane, butane, pentane and hexane.

According to another embodiment of the invention, a method of analyzing a drug or drug metabolite includes determining the isotopic composition of at least a portion of an analyte of a drug or drug metabolite in a sample according to one of the methods described herein. The method also includes comparing the isotopic composition obtained for the drug or drug metabolite to a database of isotopic compositions. The correlation between the isotopic composition obtained for the drug or drug metabolite and the database of isotopic compositions can be used to determine a property of the drug or the drug metabolite and is useful in the forensic study of diverse organic compounds.

According to another embodiment of the invention, a method of determining an amount of an anthropogenic contribution to an atmospheric concentration of an atmospheric gas includes determining the isotopic composition of at least a portion of an analyte in a sample according to one of the methods described herein. The method further includes comparing the isotopic composition obtained for the analyte to a database of isotopic compositions. The correlation between the isotopic composition obtained for the analyte and the database of the isotopic compositions can be used to determine the amount of the anthropogenic contribution to the atmospheric concentration of the atmospheric gas.

According to another embodiment, a method for the diagnosis or treatment of a disease includes determining the isotopic composition of at least a portion of an analyte in a sample from a patient according to one of the methods described herein. The method further includes comparing the isotopic composition obtained for the analyte to a database of isotopic compositions. The correlation between the isotopic composition obtained for the analyte and the database of the isotopic compositions can be used to determine a disease diagnosis or disease treatment protocol.

According to another embodiment of the invention, a method of determining a prior temperature of a sample includes determining the isotopic composition of at least a portion of an analyte in a sample according to one of the methods described herein. The method further includes comparing the isotopic composition obtained for the analyte to a database of isotopic compositions. The correlation between the isotopic composition obtained for the analyte and the database of isotopic compositions can be used to determine the prior temperature of the sample.

BRIEF DESCRIPTION OF THE DRAWINGS

These and other features and advantages of the present invention will be better understood by reference to the following detailed description when considered in conjunction with the accompanying drawings, briefly described below.

DETAILED DESCRIPTION

Figure 1:
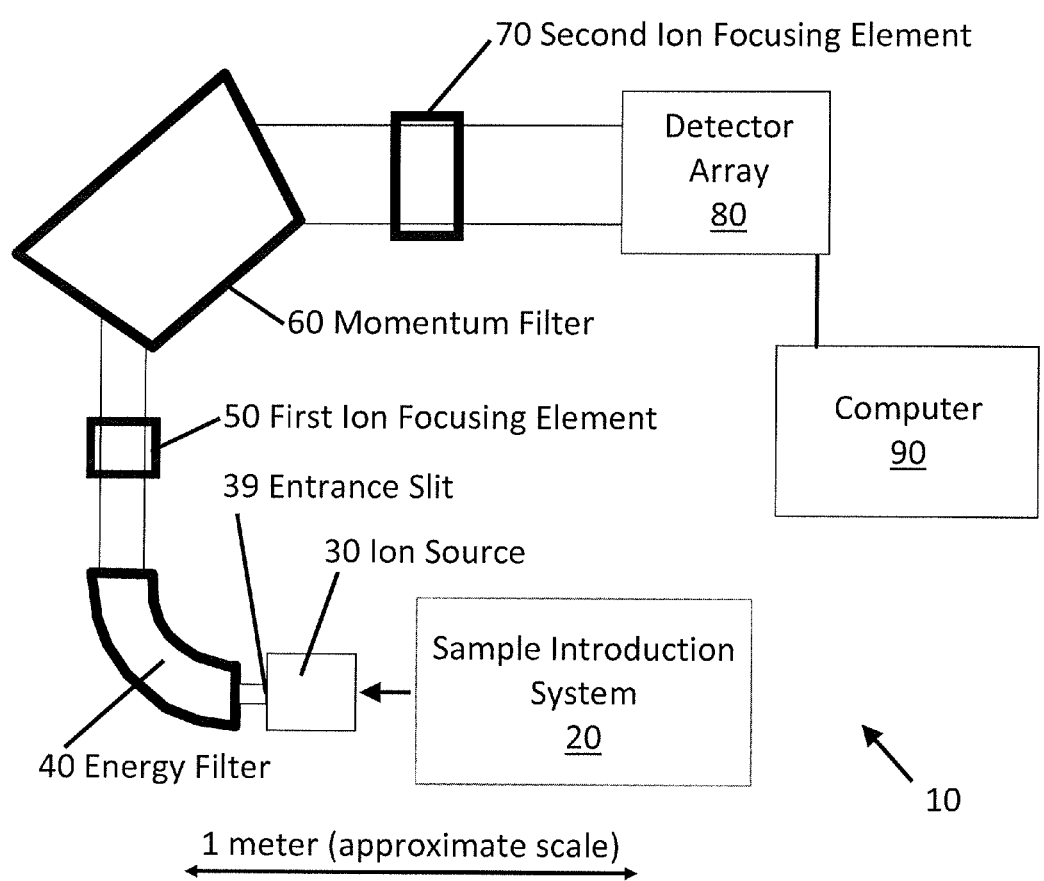
FIG. 1 is a schematic top view of a mass spectrometer according to one embodiment of the invention.

Embodiments of the present invention are directed to apparatus and methods for determining the isotopic composition (or isotopic anatomy) of an analyte, such as a volatile and/or organic molecule. For example, embodiments of the invention are directed to apparatus for measuring intensity ratios of molecular ions, fragment ions and/or adduct ions, and to methods for determining abundance ratios of isotopologues and position-specific isotopic compositions of an analyte within a sample or samples. Quantitative analysis of the relative abundances of isotopologues of molecules can be accomplished through: (1) high-resolution, multi-collector mass spectrometric analysis of molecular ions, fragment ions and/or adduct ions of such molecules (e.g., the analyte) produced by gas-source electron impact ionization; (2) calibration of a variety of relevant analytical biases through comparison of the data obtained for the sample (e.g., the analyte) with data obtained for appropriately prepared standards (e.g., reference materials); and (3) reconstruction of the original molecular isotopic structure of the analyte through integration of measured compositions of the various fragment species.

As used herein, the term "isotopologues" is used in its art recognized sense and refers to molecules that have the same chemical structure, but differ in their isotopic composition (i.e., the isotopologues have differing isotopic substituents). For example, $CH_3D$ and $CH_4$ are isotopologues of one another. As used herein, the term "multiply-substituted isotopologue" is used in its art recognized sense and refers to a molecule that includes two or more rare isotopes. For example, $^{13}CH_3D$ is a multiply-substituted isotopologue. As used herein, the term "isotopomers" is used in its art recognized sense and refers to molecules having the same chemical composition and the same kind and amounts of isotopic substituents, but differ in the molecular positions of at least some of the atoms (e.g., the positions of the isotopic substituents). For example, $CH_2D$-$CH_2$—$CH_3$ and $CH_3$—$CHD$-$CH_3$ are isotopomers of one another. Isotopomers are strictly identical at any mass resolution, and cannot be separated by their respective mass to charge ratios, since they have the same mass. As used herein, the term "cardinal mass" refers to the mass of an ion or molecule after rounding to the nearest whole number. Thus, two or more ions (including molecular ions) having the same cardinal mass (or a single cardinal mass) would have masses that each round to the same nearest whole number. Ions derived from a single sample and having the same cardinal mass may be analyzed separately using a mass spectrometer only when the mass resolving power of the mass spectrometer is sufficient to distinguish the small differences in mass that arise due to one ion containing a heavy isotope (e.g., $^{13}C$) and the other ion containing another, different heavy isotope (e.g., D). As used herein, the term "data" is used in its art recognized sense and refers to quantities obtained using the apparatus or methods described herein and can include, for example, a single ion intensity, a set of ion intensities, ratios of ion intensities, a mass spectrum and/or mass spectra.

An apparatus and/or method according to embodiments of the invention can be used in earth and environmental science (e.g., thermometry of natural compounds and developing budgets for atmospheric gases), chemistry, forensics (e.g., chemical forensics and explosives fingerprinting), biomedical research, diagnosis and treatment of diseases (e.g., drug and/or drug metabolite tracking), and hydrocarbon (e.g., oil and gas) exploration. For example, embodiments of the invention are directed to a method of identifying a potential (e.g., a high-potential) subsurface hydrocarbon deposit (e.g., an oil-field).

A mass spectrometer according to an embodiment of the invention has the ionization capabilities of a gas source isotope ratio mass spectrometer and the mass resolution, sensitivity and versatility of analyzers and detector arrays of ion microprobe and inductively coupled plasma mass spectrometers. An embodiment of the mass spectrometer is shown in FIG. 1. In this embodiment, the mass spectrometer 10 includes an entrance slit 39, an energy filter 40 (e.g., an electrostatic analyzer or "ESA") and a momentum filter 60 (e.g., a magnetic sector) configured to provide molecular analyte ions to a detector array 80. The mass spectrometer can be configured to provide a mass resolution (which is described in more detail below) of 20,000 or greater at the detector array by sequentially arranging the entrance slit, the energy filter and the momentum filter, and by appropriately selecting a width of the entrance slit, a first radius of curvature of the energy filter and a second radius of curvature of the momentum filter.

The mass resolution achieved by a mass spectrometer according to embodiments of the invention (e.g., a magnetic sector mass spectrometer) is generally proportional to the separation distance between two ion beams that the mass spectrometer can achieve for ion beams that include respective ions having masses that are different from one another. The separation distance between the ion beams is proportional to the second radius of curvature of the momentum filter (i.e., magnet), and inversely proportional to the width of each ion beam, which is proportional to the width of the entrance slit. Additionally, the highest mass resolutions can only be achieved by momentum filtering (e.g., magnetic sector mass spectrometry) if the ions being filtered by momentum have substantially uniform kinetic energy. Thus, according to embodiments of the invention, the ions are filtered by energy (e.g., by the energy filter) prior to being filtered by momentum (e.g., by the momentum filter). Accordingly, the energy filter has dimensions that are consistent with the creation of a double-focusing condition at the ion detector, given the accelerating potential of the ions as they exit the ion source and the radius of the momentum filter. For example, mass resolutions in the range of about 2,000 to about 20,000 can be achieved if the entrance slit has a width of about 250 μm to about 5 μm, respectively, the ions are accelerated to 5 keV after exiting the ion source, the first radius of curvature of the energy filter is about 20 cm to about 25 cm, the ions are further accelerated by an additional 5 keV after the energy filter, and the second radius of curvature of the momentum filter (e.g., magnetic sector) is about 20 cm to about 25 cm. In one embodiment, the width of the entrance slit is about 5 μm, the first radius of curvature of the energy filter is about 22 cm, and the second radius of curvature of the momentum filter is about 23 cm.

As shown in FIG. 1, the mass spectrometer 10 can also include a sample introduction apparatus 20, which is configured to provide an analyte gas (or other gases) to an ion source 30. The ion source is configured to convert the analyte gas (or other gases, such as various reference materials described below) to ions (e.g., molecular analyte ions). The ion source produces the ions as a first output (e.g., a first output of molecular analyte ions). As the ions exit the ion source, they encounter the entrance slit 39, which can be included as a component of the ion source or can be connected to the ion source. The entrance slit is configured to guide the first output of molecular analyte ions along a path.

The energy filter 40 (e.g., the ESA) is positioned along the path downstream from the entrance slit 39 and is configured to receive the first output of molecular analyte ions, which have energy levels. The energy filter has a first radius of curvature along the path and is configured to filter the molecular analyte ions of the first output according to their energy levels and produce a second output of molecular analyte ions. The energy filter can be any suitable device that can filter ions according to their energy levels, such as an ESA.

A first ion focusing element 50 can be included along the path between the energy filter 40 and the momentum filter 60. The first ion focusing element is configured to focus the second output of molecular analyte ions along the path to the momentum filter. The first focusing element can be any suitable device capable of focusing the second output of molecular analyte ions, such as a magnetic lens (e.g., a quadrupole or higher format lens).

The momentum filter 60 is positioned along the path downstream from the ion source 30, the entrance slit 39, the energy filter 40 and the first ion focusing element 50, and is configured to receive the second output of molecular analyte ions. The momentum filter has a second radius of curvature along the path and is configured to filter the second output of molecular analyte ions according to their momenta and produce a third output of molecular analyte ions. The momentum filter can be any suitable device that can filter ions according to their momenta, such as a magnetic sector.

A second ion focusing element 70 can be included along the path between the momentum filter 60 and the detector array 80. The second ion focusing element is configured to focus the third output of molecular analyte ions along the path to the detector array. The second ion focusing element can be any suitable device capable of focusing the third output of molecular analyte ions, such as a magnetic lens (e.g., a quadrupole or higher format lens).

The detector array 80 is positioned downstream of the momentum filter 60 (and the second ion focusing element 70) and is configured to receive the third output of molecular analyte ions. The detector array may be any suitable device or combination of devices capable of concurrently detecting two or more molecular analyte ions of the third output of molecular analyte ions, of which the two or more molecular analyte ions have masses that are different from one another (and mass to charge ratios that are different from one another).

The mass spectrometer 10 can be configured to provide the third output of the molecular analyte ions to the detector array 80 at a mass resolution (which is described in more detail below) of 20,000 or greater. For example, the width of the entrance slit 39 and the first and second radii of curvature of the energy filter and momentum filter can be selected to provide a mass resolution at the detector array of 20,000 or greater. In one embodiment, the third output of molecular analyte ions includes at least two ion beams and respective molecular analyte ions of the ion beams have respective masses that differ from one another by about 1 atomic mass unit, and the width, first and second radii of curvature, and detector array are configured to resolve and concurrently detect the at least two ion beams and to distinguish between molecular analyte ions within each ion beam at one part in 20,000. The detector array is configured to concurrently detect the at least two molecular analyte ions. The detector array can be connected to a computer 90, which can be configured to acquire data from the detector array and to process the data. As described in more detail below, the computer can also be configured to control various features of the mass spectrometer, such as the detector array.

Figure 2:
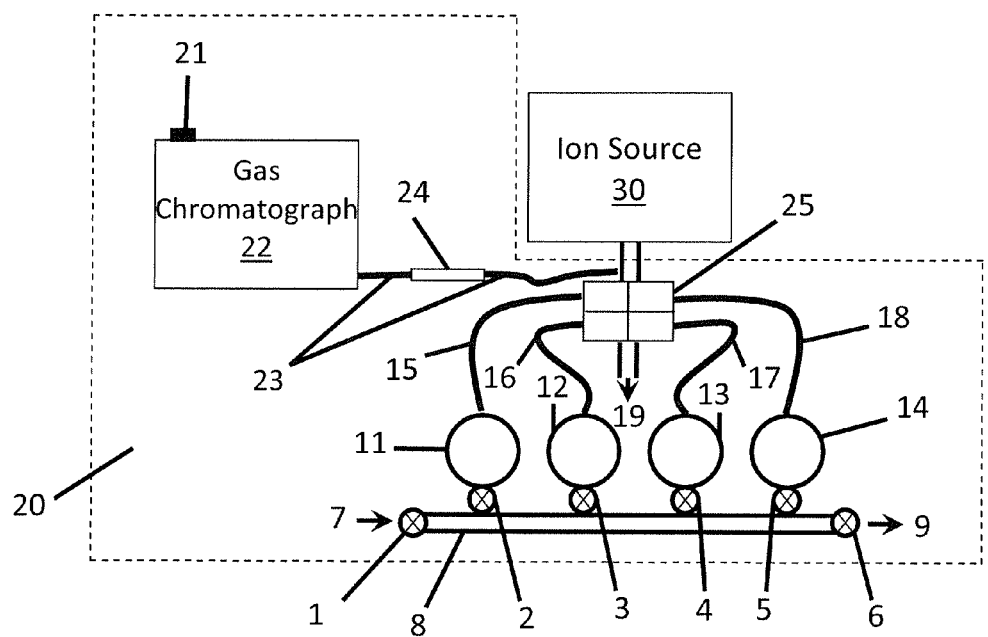
FIG. 2 is a schematic view of a sample introduction system for a mass spectrometer according to one embodiment of the invention.

Embodiments of the individual components of the mass spectrometer will now be described in more detail. FIG. 2 shows an embodiment of the sample introduction system 20 coupled to the ion source 30 through five separate conduits (e.g., capillaries). Any of the following conduits can be heated to facilitate the delivery of an analyte or reference material to the ion source. The sample introduction system is configured to provide analyte(s) or reference material(s) to the ion source as a neutral gas. The analyte(s) or reference material(s) can be introduced to the ion source as a pure gas through a viscous capillary bleed (e.g., a flow of gas through a capillary column) or they can be entrained in a flow (e.g., a continuous flow or a pulsed flow) of any suitable carrier gas (e.g., helium gas).

The analyte described herein can be any suitable gas or volatile compound (e.g., a volatile organic compound) that can be translated through a confined tube as a pure gas or as an analyte entrained in a carrier gas. Any analyte that can be suitably analyzed using the mass spectrometer can be used. For example, the analyte can be, or can be derived from, any suitable gas, volatile compound, semi-volatile liquid or sublimable solid. For example, volatile compounds can include any organic compound that can be suitably measured or analyzed in the mass spectrometer, such as, but not limited to alkanes (e.g., n-alkanes), oxygenates, aromatic compounds, heteroaromatic compounds, cyclic compounds, heterocyclic compounds, and the like Additionally, the analyte can be derived from a sample that is unsuitable for analysis in the mass spectrometer, such as a non-volatile liquid organic compound or liquid or non-sublimable solid. That is, a sample that is otherwise incapable of being analyzed in the mass spectrometer can be converted into an analyzable sample by preparing an analyte that is a derivative or reaction product of the sample and that is capable of being analyzed in the mass spectrometer, and thereby the derivative or reaction product can be used as a proxy for the sample that would be otherwise unsuitable for analysis or measurement. The analyte can be any suitable compound that can be introduced by the sample introduction system 20 into the ion source 30 as a gas.

In the embodiment shown in FIG. 2, the sample introduction system includes an introduction tube 8 configured to receive pure sample gases 7, such as analyte or reference material gases. A first valve 1 (e.g., a first high-vacuum pneumatic valve) is configured to control the flow of the gases into the introduction tube. The introduction tube is further coupled to four sets of valves, bellows and conduits (e.g., capillaries) arranged in parallel and coupled to a valve block configured to selectively couple the introduction tube to the ion source through each set of valves, bellows and conduits.

As shown in FIG. 2, the introduction tube 8 is coupled to a second valve 2, a third valve 3, a fourth valve 4, a fifth valve 5 and a sixth valve 6, each of which can be a high-vacuum pneumatic valve. The second through fifth valves are each configured to selectively couple the introduction tube to a first bellows 11, a second bellows 12, a third bellows 13, and a fourth bellows 14, respectively. The first through fourth bellows 11-14 are each coupled to a first conduit 15, a second conduit 16, a third conduit 17, a fourth conduit 18, respectively. The first through fourth conduits 15-18 (e.g., the first through fourth capillaries) are coupled to a valve block 25 (e.g., a change-over valve block), which is coupled to the ion source 30. The sixth valve is coupled to a high-vacuum system 9.

By appropriately selecting the first through sixth valves 1-6, a gas, such as an analyte, analytes or reference material, can be introduced into the introduction tube and confined therein. For example, the first valve 1 can be opened to introduce a gas to the introduction tube, and one of the second through fifth valves 2-5 can be selected to couple the introduction tube to one of the first through fourth bellows 11-14, respectively, to thereby provide the gas to the selected bellows. By opening the first valve, a gas can be introduced into the introduction tube, and by opening the second valve 2, the gas can be provided to the first bellows 11. From the first bellows, the gas can then be provided to the first conduit 15 (e.g., the first capillary), which is coupled to the valve block 25. The valve block can selectively couple the first conduit to the ion source 30. Thus, the sample introduction system 20 can provide a gas to the ion source through the first valve, the introduction tube, first bellows, first conduit and change-over block. Similarly, other gases can be provided to the ion source through the first valve, introduction tube, third through fifth valves, second through fourth bellows, second through fourth conduits and valve block. The sixth valve is configured to selectively couple the introduction tube to the high-vacuum (HV) system 9 to evacuate and purge the introduction tube when switching between gases. As shown in FIG. 2, the valve block is also selectively coupled to an HV system 19 configured to evacuate and purge the valve block when switching between gases. The HV systems 9 and 19 can be the same or different. Any of the above-described introduction tube, first through sixth valves, first through fourth bellows and valve block can be heated to facilitate delivery of an analyte or reference material to the ion source.

In the embodiment shown in FIG. 2, the sample introduction system 20 further includes a gas chromatograph 22 coupled to the ion source 30 through a fifth conduit 23 (e.g., a fifth capillary) including an open split 24. A sample can be injected into the gas chromatograph through an injector 21 and the sample can be separated by the gas chromatograph to provide a purified analyte (e.g., a specific compound or specific set of compounds) to the fifth conduit, which transmits the analyte through the open split to the ion source. Any suitable gas chromatograph can be used. The analyte can be entrained in a carrier gas flow (e.g., He) that flows through the gas chromatograph, the fifth conduit and the open split to the ion source. The open split is configured to allow the sample introduction system to provide equivalent conditions to the ion source regardless of whether an analyte is provided by the chromatograph to the fifth conduit. The fifth conduit and/or open split can be heated to facilitate delivery of an analyte or reference material to the ion source.

The above-described first through fifth conduits 15-18 and 23 are configured to provide two or more streams of matter (e.g., analyte(s) or reference material(s)) to the ion source 30. The conduits can be configured to accommodate: (1) a sample of purified compounds that are gases at room temperature; (2) a capillary bleed of carrier gas (e.g., He delivered through the open split 24 and fifth conduit 23); and (3-5) three separate reference materials (e.g., reference gases) that differ from one another in their isotopic compositions by known amounts. With respect to (2), the capillary bleed of carrier gas can be configured to serve as the carrier gas for volatile organic compounds, such as volatile organic compounds introduced through the gas chromatograph 22. Each of the conduits (e.g., capillaries) described above is capable of introducing analyte(s) or reference material(s) to the ion source as a stream of matter and of being separately and independently selected.

As discussed in more detail below, in some embodiments, measurements of an analyte (or analytes) are standardized to concurrently analyzed standards (e.g., reference materials) and, therefore, the sample introduction system 20 can be configured to deliver the analyte (or analytes) to the ion source 30 through two or more separate conduits described above. Using the sample introduction system, reference materials can be preselected such that inter-comparison of the reference materials can be used to determine the mass discrimination of the mass spectrometer source, the reaction constants for relevant fragmentation/adduct reactions at the ion source, and the linearity of the mass spectrometer detector system.

Figure 3:
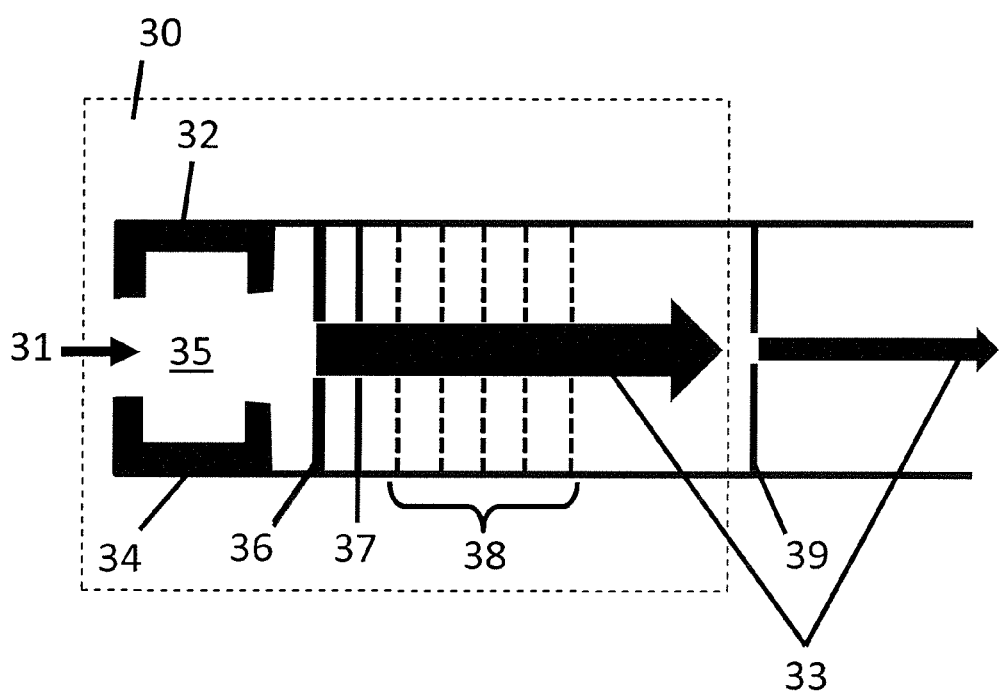
FIG. 3 is a cutaway schematic view of an ion source and entrance slit aperture for a mass spectrometer according to one embodiment of the invention.

The sample introduction system 20 can be any apparatus that is suitable for use with a gas source isotope ratio mass spectrometer, such as, for example, a mercury bellows, an automated mechanical bellows (e.g., the dual inlet systems of the mass spectrometers available from Nu Perspective or the MAT-253 mass spectrometer available from Thermo Fisher Scientific, Inc.), a He-purged carrier gas system that interfaces with a capillary bleed through an open split, or the like. Any apparatus capable of delivering the analyte with flow sufficient to support pressures at the ion source 30 on the order of $10^{-6}$ mbar can be used. Backing pressures of several mbar to about 1 bar are generally achieved using a capillary bleed having an interior diameter of tens to hundreds of microns. In some embodiments, the mass spectrometer 10 includes a modified version of the "front end" of the MAT-253 mass spectrometer available from Thermo Fisher Scientific, Inc., including a sample introduction system including 4 bellows and a carrier-gas port (as described above with respect to FIG. 2), and a modified ion source 30 as shown in FIG. 3. The sample introduction system and ion source can be modified to have the characteristics described herein and to be compatible with the other components of the mass spectrometer described herein. For example, in one embodiment, the sample introduction system 20 includes each of the components of the sample introduction system of the MAT-253 mass spectrometer available from Thermo Fisher Scientific, Inc., with the components of the sample introduction system physically rearranged to fit within a cabinet that differs in size and shape from that of the MAT-253.

In the embodiment shown in FIG. 3, the ion source includes an ionization chamber 35 between a trap 32 (e.g., an anode) and a filament 34 (e.g., a hot cathode). The ion source can further include electrostatic lenses and apertures generally similar to those used in other gas source mass spectrometers. For example, in FIG. 3, the ion source further includes an extraction lens 36, a shield 37, and focusing/grounding elements 38. Neutral gas 31 (e.g., analyte or reference material gas) enters the ionization chamber and molecular ions are generated by electron impact. The molecular ions are then extracted as an ion beam 33, accelerated and focused by the extraction lens, shield, and focusing/grounding elements. The ion source can provide molecular ions with an initial acceleration of about 5 kV. In FIG. 3, the entrance slit 39 is adjacent to the ion source, and the ion beam is further focused or narrowed as it exits the ion source through the entrance slit.

The ion source 30 can be any suitable ion source, such as those including an electron-impact ionization chamber resembling the Nier-type ion source used in existing gas-source isotope ratio mass spectrometers. For example, the ion source can be a Nier-type ion source available from Nu Perspective or Thermo Fisher Scientific, Inc. (e.g., the ion source of the MAT-253 mass spectrometer) that has been modified by expanding the range of electron impact energy to extend down to at least 5 eV, rather than the standard lower limit of 50 eV. In one embodiment, the ion source 30 is the ion source of the MAT-253 mass spectrometer available from Thermo Fisher Scientific, Inc., machined to fit within a housing that differs in size and shape from that of the MAT-253, and machined to fit together with the other components of the mass spectrometer.

An ion source capable of providing an electron impact energy of less than 50 eV provides improved control over the fragmentation spectrum of the molecular ions as compared to an ion source that has a 50 eV lower limit on electron impact energy. The ion source can be configured to have a voltage potential between the source filament (e.g., the filament 34) and the housing of the ionization chamber (e.g., the trap 32) that is adjustable in a range of at least 5 eV to less than or equal to 150 eV. For example, the ion source can be capable of providing an electron impact energy of less than 50 eV, such as an ion source that is configured to provide an electron impact energy of about 5 eV to about 150 eV, or about 25 eV to about 150 eV.

As shown in FIG. 3, the entrance slit 39 is the last aperture encountered by the ion beam 33 as it exits the ion source 30. The entrance slit can be adjacent to the ion source, and it can be between the ion source and the detector array 80. In some embodiments, the entrance slit has a variable aperture. For example, the entrance slit can be adjustable to a width in a range of about 10 µm to about 250 gµm, such as a width of 5 gµm to about 250µ, or a width of about 5 µm. The entrance slit can be adjustable, either continuously or through movement of two or more fixed-width apertures (having the same or different fixed-widths), such that the ion beam width can reach the intended mass resolution of about 20,000 or greater at the detector array. For example, the entrance slit width can be achieved by using two or more slits movable relative to one another to achieve the desired width. Thus, the width of the entrance slit can vary between 5 µm and about 250 µm by way of a mechanical device that translates slits of variable width in and out of the path of the ion beam through the mass spectrometer analyzer. In some embodiments, when the mass spectrometer has overall dimensions and ion optics similar to those of conventional high-resolution inductively coupled mass spectrometers, an entrance slit as small as 5 to 10 gµm can be used.

Referring back to FIG. 1, the energy filter 40 is configured to receive the first output of molecular analyte ions from the entrance slit 39. The energy filter can be any suitable device capable of separating ions according to their energy levels, such as an electrostatic analyzer. The energy filter can be dynamically pumped to maintain the interior of the energy filter under high-vacuum. The energy filter can have a first radius of curvature of about 20 cm to about 25 cm, which may be equal (or roughly equal) to the second radius of curvature of the momentum filter, provided that the kinetic energy of the ions entering the energy filter is about one half of the kinetic energy that the ions will have when entering the momentum filter. For example, a first radius of curvature of the energy filter of about 20 cm to about 25 cm will provide suitable mass resolution at the detectors if the ions are accelerated to one half of their final energy prior to entering the energy filter and the ions are then accelerated to their full final energy after energy filtering. For example, a first radius of curvature can be about 22 cm. One or more electrostatic lenses may be used to shape, focus and/or center the ion beam before the ion beam enters the energy filter. Similarly, one or more electrostatic lenses may be used to shape, focus and/or center the ion beam between the energy filter and the momentum filter, and/or between the momentum filter and the detectors. The energy filter can provide the first output of molecular analyte ions with about 5 kV of acceleration in addition to the acceleration provided by the ion source 30. As an example, the energy filter can be the energy filter of a Neptune mass spectrometer or Triton mass spectrometer (each of which are available from Thermo Fisher Scientific, Inc.), modified to have the above-described characteristics and to be compatible with the other components of the mass spectrometer described herein. For example, in one embodiment, the energy filter is the electrostatic analyzer of the Neptune mass spectrometer available from Thermo Fisher Scientific, Inc.

In FIG. 1, the energy filter 40 is configured to produce a second output of molecular analyte ions. The second output can pass through the first ion focusing element 50, which can function as a transfer lens (e.g., a quadrupole or higher format lens). The first ion focusing element can be configured to focus the second output of molecular ions. For example, in one embodiment, the first ion focusing element is one of the ion focusing elements of the Neptune mass spectrometer available from Thermo Fisher Scientific, Inc.

The momentum filter 60 is positioned downstream from the energy filter 40 and the first ion focusing element 50, and is configured to receive the second output of molecular analyte ions. The momentum filter has a second radius of curvature and is configured to filter the molecular analyte ions of the second output according to their momenta. The momentum filter produces a third output of molecular analyte ions. The momentum filter can have a second radius of curvature of about 20 cm to about 25 cm. For example, the momentum filter can include a magnet having a second radius of curvature of about 23 cm. As an example, the momentum filter can be the momentum filter of a Neptune mass spectrometer or Triton mass spectrometer (each of which are available from Thermo Fisher Scientific, Inc.), modified to have the above-described characteristics and to be compatible with the other components of the mass spectrometer described herein. For example, in one embodiment, the momentum filter is the magnetic sector of the Neptune mass spectrometer available from Thermo Fisher Scientific, Inc.

A second ion focusing element 70 can be positioned downstream of the momentum filter 60. The second ion focusing element can be configured to focus the third output of molecular analyte ions. For example, the second ion focusing element can be a "zoom" lens, such as a dispersion quadrupole or higher format lens. In some embodiments, the second ion focusing element has "zoom" optic capability (±5% mass range) and is configured to provide 2× magnification at the image plane of the detector array 80. For example, in one embodiment, the second ion focusing element is one of the ion focusing elements of the Neptune mass spectrometer available from Thermo Fisher Scientific, Inc.

As shown in FIG. 1, the detector array 80 is positioned downstream of the momentum filter 60 and the second ion focusing element 70. At least a portion of the molecular ions (e.g., analyte ions, reference material ions, etc.) that pass through the momentum filter and second ion focusing element are detected at the detector array. For example, the detector array can be configured to receive the third output of molecular analyte ions from the momentum filter.

Figure 4:
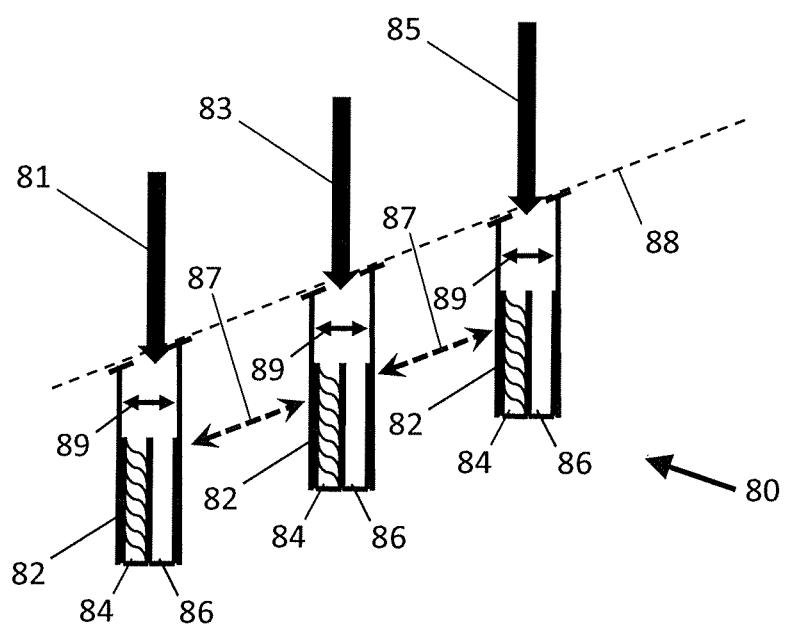
FIG. 4 is a cutaway schematic view of a detector array for a mass spectrometer according to one embodiment of the invention.

The detector array 80 can be a multi-collector array including two or more detectors (e.g., 5 to 10 detectors) capable of faraday-cup or ion counting detection at each of several positions. For example, FIG. 4 is a partial schematic view of the detector array 80 including detectors 82. As shown in FIG. 4, the ion current of the ion beams 81, 83 and 85 arriving at the respective detectors is registered through either an electron multiplier 84 (or ion counting system having similar performance characteristics) or faraday cup 86 current monitoring system to enable quantitative analysis over a large dynamic range in sensitivity at each mass position. The ion beams can include molecular analyte ions or reference material ions, and the ions of the respective ion beams have masses that are different from one another. For example, the third output of molecular analyte ions can include the ion beams 81, 83 and 85.

Both the position and sensitivity (e.g., ion counting vs. faraday cup current measurement) of at least one detector 82 can be controlled in an automated fashion (e.g., through the computer 90 of FIG. 1) so that the collection characteristics of the detector can be adjusted on time scales of minutes, without disturbing the delivery of analyte to the mass spectrometer source or the vacuum within the mass spectrometer. The foregoing switching capability is beneficial, because most analyses of interest benefit from comparison of measured ratios for two or more molecular or fragment ions derived from the same analyte species (see examples, below).

In some embodiments, the detector array 80 can be reconfigured over the course of measurements made on a single sample (e.g., a single analyte), and the reconfiguration can be both rapid and convenient. At least one of the detectors 82 is capable of movement relative to the other detectors such that the relative positions of detected ions can be adjusted. For example, in FIG. 4, the detectors can vary their relative spacing as shown by the arrows 87. The detectors can vary their position along the focal or image plane of the mass spectrometer, which is indicated by the dashed line 88. The detectors can be sufficiently mobile to permit rapid reconfiguration to achieve a wide range of relative and absolute mass positions, up to a mass to charge ratio of about 300. Reconfiguration of detector position can be motorized and automated, and can be performed through stepper motors or analogous mechanical devices, which can be controlled and powered remotely through vacuum feedthroughs.

Switching between ion counting and current monitoring detectors at each detector position can be achieved through electrostatic deflectors at the exit slit positioned before each detector position. The arrows 89 indicate the electrostatic deflection that can be used to switch between detection by ion counting (e.g., detection by the electron multiplier 84) and detection by current measurement (e.g., detection by the faraday cup 86).

In one embodiment, the detector array 80 includes seven detectors 82, six of which are movable. Each detector includes a faraday cup (FC) and an electron multiplier (EM), and each detector is switchable between FC and EM measurement. Additionally, signals can be collected from each FC and EM concurrently (or simultaneously). Detector signals are converted to digital measures of intensity (e.g., ion current or counts-per-second rates) using digital-to-analog (DAC) circuits common to the detector systems of several commercially available isotope ratio mass spectrometers, and then delivered to the computer 90 (shown in FIG. 1) capable of storing relative ion beam intensities for later data processing. In one embodiment, the detector array further includes a retarding potential quadrupole (RPQ) lens upstream of the central detector, such that ions pass through the RPQ lens prior to arriving at the central detector.

Examples of suitable detector arrays include the detector arrays of the Cameca ims 1280 microprobe and NanoSIMS ion probes, each available from Cameca, Société par Actions Simplifiée, and the detector array of the Triton thermal ionization mass spectrometer, available from Thermo Fisher Scientific, Inc.

According to embodiments of the invention, the above-described components can be arranged to provide a double-focusing, normal-geometry sector mass spectrometer having an ion beam size, mass separation and system stability sufficient to achieve a mass resolution at the detector array of 20,000 or greater (mass/$\Delta$M, according to the 5%-95% definition, which is described in more detail below). The mass spectrometer can have the following capabilities: a vacuum under analytical conditions of not more than $10^{-8}$ mbars; useful ion yield of not less than 1 ion per $5 \times 10^4$ molecules at the highest mass resolution; a mass range of about 2 to about 300 atomic mass units ("AMU"), such as a mass range of about 2 to about 280 AMU; a mass resolution on the order of 20,000 (according to the mass/$\Delta$M, 5%-95% definition, which is described in more detail below); and abundance sensitivity of not more than $10^{-6}$. Prior art mass spectrometers are not capable of multi-collection of molecular analyte ions (e.g., concurrently detecting two or more molecular analyte ions, the molecular analyte ions having different masses) generated by electron impact ionization at a mass resolution of 20,000 or greater (as described in more detail below). Embodiments of the invention further include a Nier-type gas source and associated inlet system to the analyzer, such that high-resolution multi-collector mass spectrometry can be performed on molecular ions generated by electron impact on gases and volatile compounds (e.g., volatile organic compounds). The mass spectrometer has a mass range sufficient for analyzing ions of large volatile organic molecules (e.g., phytane) and their associated fragments. When the mass spectrometer has a mass resolution at the detector array of 20,000 or greater, the mass spectrometer can resolve isobaric interferences among isotopologues of organic molecules (e.g., internal isobars, such as isotopologues having the same cardinal mass), their fragments, their adducts, and contaminant species (e.g., contaminants having the same cardinal mass as the molecular analyte ion or molecular analyte fragment ion being measured). These features are not found in other mass spectrometer designs that are also capable of multiple simultaneous collection of two or more ion beams.

Methods

Figure 5:
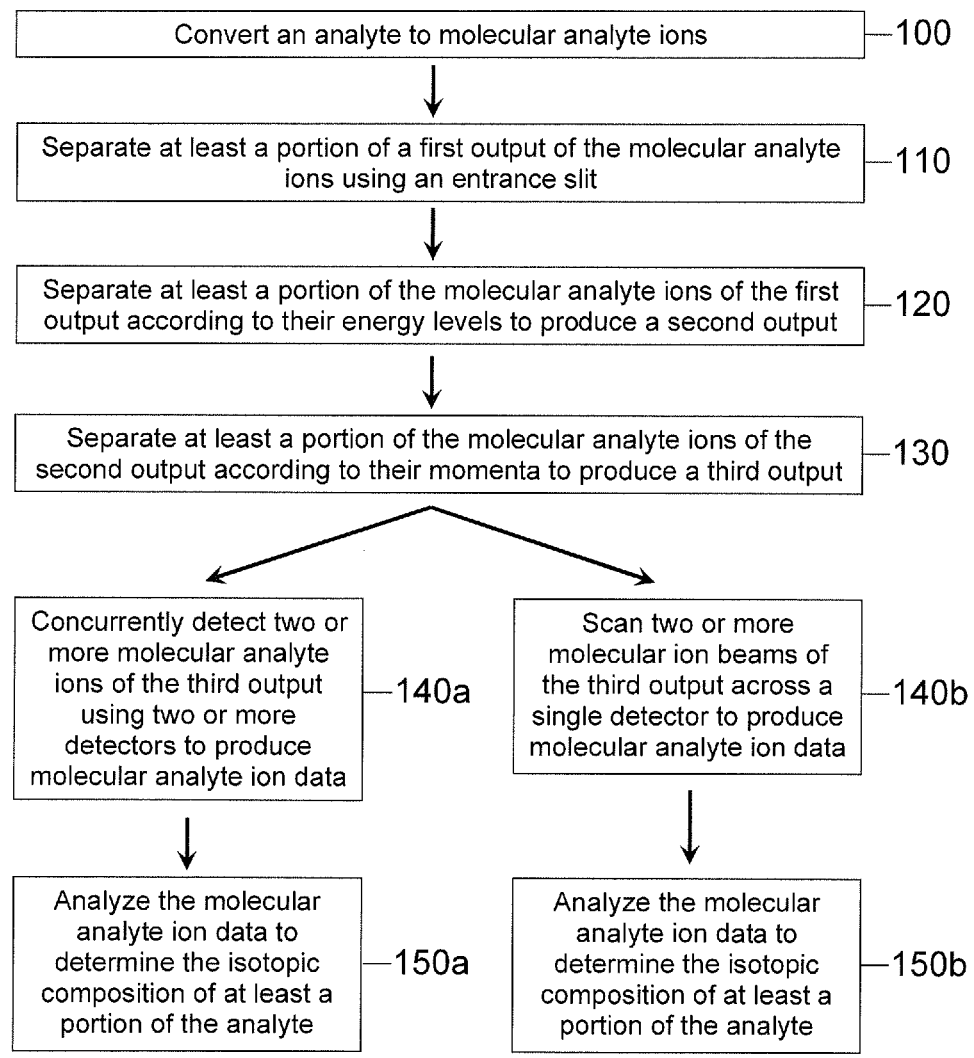
FIG. 5 is a flowchart showing methods for determining the isotopic composition of an analyte in a sample according to embodiments of the invention.

Embodiments of the invention are also directed to methods for determining the isotopic composition of a compound (e.g., an analyte), such as methods of using the above-described mass spectrometer 10. For example, FIG. 5 is a flow chart illustrating a method for determining the isotopic composition of an analyte in a sample. The method includes (100) converting an analyte to molecular analyte ions. The analyte can be converted to the molecular analyte ions using an ion source of a mass spectrometer (e.g., the ion source 30 described above). The ion source can produce the molecular analyte ions from the analyte. The method further includes (110) separating at least a portion of the molecular analyte ions using an entrance slit to produce a first output of molecular analyte ions. The molecular analyte ions from the ion source can be separated using the above-described entrance slit 39 to produce the first output. As described above, the entrance slit 39 can have an adjustable width. The width can be adjusted to vary the separation of the molecular analyte ions from the ion source and to adjust the mass resolution of the spectrometer at the detector array (e.g., the above-described detector array 80).

The method of FIG. 5 also includes (120) further separating at least a portion of the molecular analyte ions of the first output according to their energy levels to produce a second output. The further separating of the molecular analyte ions of the first output can be accomplished using the above-described energy filter 40 (e.g., the electrostatic analyzer). The degree of the further separation of the molecular analyte ions by the energy filter depends upon the first radius of curvature of the energy filter. Thus, as described above, the first radius of curvature of the energy filter affects the mass resolution of the spectrometer 10 at the detector array 80. The energy filter can have any of the above-described first radii of curvature. The energy filter produces the above-described second output of the molecular analyte ions.

The method further includes (130) separating at least a portion of the molecular analyte ions of the second output according to their momenta to produce a third output. The above-described momentum filter 60 (e.g., the magnetic sector) can be used to separate the molecular analyte ions of the second output according to their momenta. The degree of separation of the molecular analyte ions by the momentum filter depends upon the second radius of curvature of the momentum filter. Thus, as described above, the second radius of curvature of the momentum filter affects the mass resolution of the spectrometer 10 at the detector array 80. The momentum filter can have any of the above-described second radii of curvature. The momentum filter produces the above-described third output of the molecular analyte ions.

Multi-Collection/Detection

The method shown in FIG. 5 further includes (140) concurrently detecting (e.g., multi-collection) two or more molecular analyte ions of the third output to produce molecular analyte ion data, the two or more molecular analyte ions having respective masses that are different from one another (and respective mass to charge ratios that are different from one another). As shown in FIG. 5, there are two different approaches to multi-collection.

In the first approach (140a), the two or more molecular analyte ions of the third output are detected using two or more detectors to produce the molecular analyte data. This embodiment is referred to as "parking," since each of the molecular ion beams is "parked" at one detector. According to this embodiment, the analyte may be introduced to the ion source 30 by the sample introduction system 20 as a continuous flow or as a time resolved pulse. Concurrent detection by parking is suitable for detecting molecular ions having respective masses that differ by at least 1 AMU. Molecular ions that differ by less than 1 AMU may not be sufficiently resolved to be concurrently detected at separate detectors.

Figure 6:
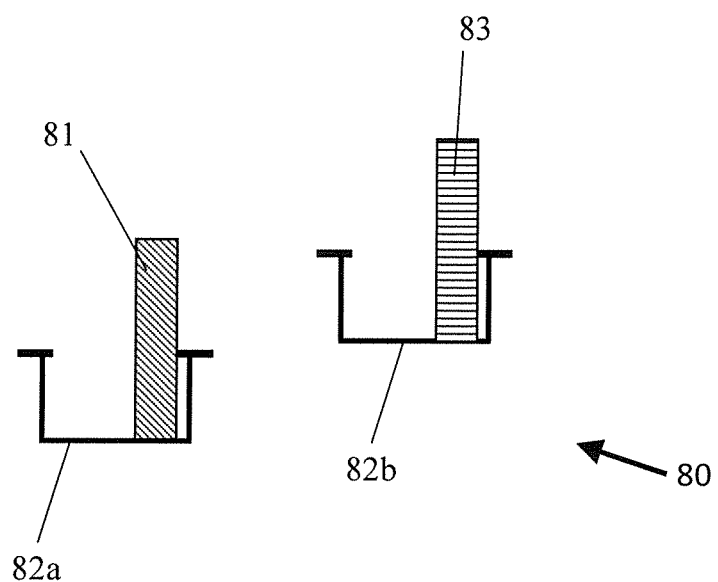
FIG. 6 is a partial schematic view of two detectors of a detector array concurrently detecting two molecular ion beams according to an embodiment of the invention.

According to this embodiment, the two or more molecular ions (e.g., molecular analyte ions) differ from one another by at least 1 AMU and can be concurrently (or simultaneously or quasi-simultaneously) detected in two separate detectors. FIG. 6 shows an example of concurrent detection by "parking" in which a first molecular ion beam 81 is detected at a first detector 82a and a second molecular ion beam 83 is concurrently detected at a second detector 82b. The intensity ratio of these two separately registered (e.g., detected) signals at any one time is the measure of the abundance ratio of the two relevant isotopic species (e.g., the respective molecular ions). The intensities detected (or registered) for the first ion beam 81 and second ion beam 83 are each recorded and averaged over a specified period of time (generally seconds). In FIG. 6, the first detector 82a and the second detector 82b are part of the same detector array 80.

This method of concurrent (or simultaneous or quasi-simultaneous) detection of ions by "parking" can be employed when the intensities of the ion beams exiting the ion source do not vary substantially over time, for example when delivering a stable (e.g., continuous) flow of gas to the ion source through a capillary bleed, or when the intensities of the ion beams vary through time, for example when analyte is delivered to the ion source as a brief pulse in a helium carrier gas stream. This method also further includes (150a) analyzing the molecular analyte ion data to determine the isotopic composition of at least a portion of the analyte. Other ions (e.g., reference material ions) can also be analyzed in the mass spectrometer in a similar manner.

In the second approach (140b), the two or more molecular analyte ions are detected by scanning the molecular analyte ions (or ion beams including the respective molecular analyte ions) across at least one detector. In some embodiments, scanning at least one molecular analyte ion beam across at least one detector produces a change in a detected signal intensity as masses of molecular analyte ions detected by the detector change at an amount of one part in 20,000. This method is referred to as "peak scanning," since the ion beams are scanned across a detector. This method of scanning can be employed when the analyte is delivered to the ion source 30 from the sample introduction system 20 as a continuous flow (e.g., through a capillary bleed that varies little in flow rate over time). This method of scanning the ion beams across a single detector is unsuitable, however, for analyses of brief pulses of analyte, such as those delivered to the ion source as components of a helium carrier gas.

Figure 7A:
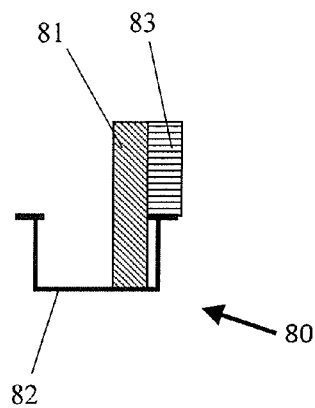
FIGS. 7A-D are partial schematic views showing two molecular ion beams being scanned across a single detector.
Figure 7B:
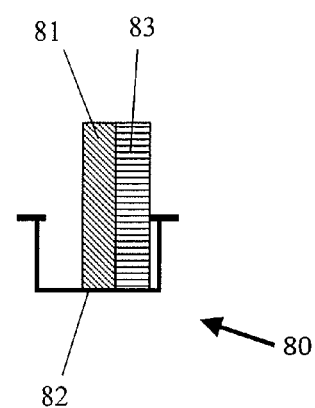
Figure 7C:
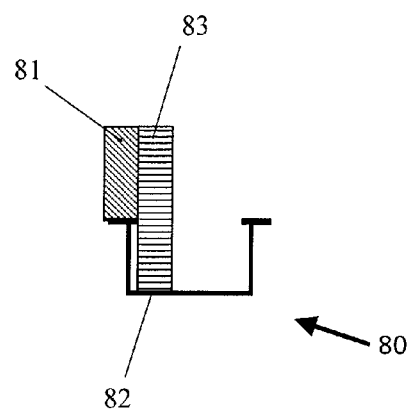
Figure 7D:
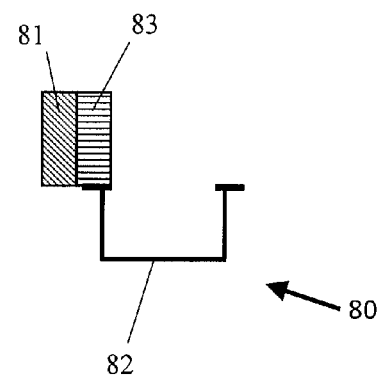
Figure 7E:
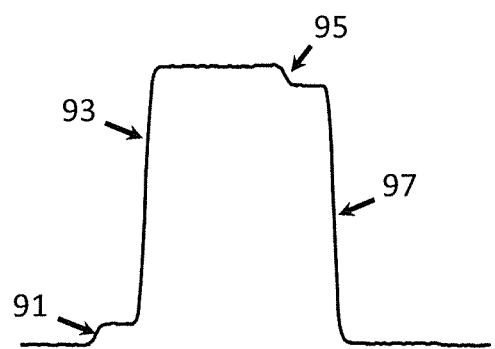
FIG. 7E is a graph showing the resultant mass spectrum.

FIGS. 7A-D illustrate the scanning of a first molecular ion beam 81 and a second molecular ion beam 83 across a single detector 82 of a detector array 80. FIG. 7E illustrates the mass spectrum that results from the scanning of the ion beams across the single detector in FIGS. 7A-D. As shown in FIG. 7A, the first molecular ion beam enters the detector first. In the mass spectrum of FIG. 7E, the first molecular ion beam is shown entering the detector at 91. Then, as shown in FIG. 7B, the second molecular ion beam enters the detector, resulting in both ion beams being detected concurrently (or simultaneously) in the detector. The second molecular ion beam is shown entering the detector at 93 of the mass spectrum of FIG. 7E, at which point the measured signal is a composite signal that includes a contribution from each of the first and second molecular ion beams. Then, the first molecular ion beam exits the detector as shown in FIG. 7C. At this point only the second molecular ion beam is detected in the detector. The first molecular ion beam is shown leaving the detector at 95 of the mass spectrum of FIG. 7E. Then, as shown in FIG. 7D, the second molecular ion beam exits the detector. The second molecular ion beam is shown leaving the detector at 97 of the mass spectrum of FIG. 7E.

Figure 7F:
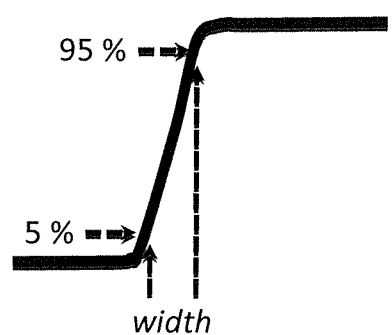
FIG. 7F is a schematic view showing the components of a signal intensity used for calculating mass resolution.

FIG. 7F illustrates the portions of a measured signal intensity that can be used to calculate the mass resolution of the mass spectrometer at the detector array. In FIG. 7F, 90%

(5%-95%) of the measured signal intensity for a particular mass is contained in the width $\Delta M$ between the two vertical arrows. The mass resolution can be calculated by dividing the mass of the ion measured by the width $\Delta M$. Accordingly, as used herein, the term "mass resolution" refers to the value calculated by dividing the mass of the ion measured by the width $\Delta M$ that contains 90% of the measured signal intensity.

The above-described scanning results in a time-varying detected ion beam intensity in the detector across which the ion beams are scanned, with an example of a resultant mass spectrum shown in FIG. 7E. The scanning can take place over a time period of seconds or minutes. The ion beams can be scanned by adjusting the accelerating potential of the ion beams (e.g., by adjusting the accelerating potential of the ion source 30 or the energy filter 40) or by adjusting the magnetic field strength of the momentum filter 60 (e.g., by adjusting the intensity of a current delivered to an electromagnet included in the momentum filter).

The peak scanning method of detecting ions can be employed when the ion beams include respective ions that have similar, but not identical, mass to charge ratios (e.g., the respective ions each have the same cardinal mass but are at least partially discriminated from one another in the mass spectrometer analyzer). Accordingly, the peak scanning approach can be applied when the molecular analyte ions have respective masses that differ from one another by less than 1 AMU. The peak scanning approach can also be applied when the molecular analyte ions have respective masses that differ from one another by at least 1 AMU (or more than 1 AMU). This method also further includes (150b) analyzing the molecular analyte ion data to determine the isotopic composition of at least a portion of the analyte. Other ions (e.g., reference material ions) can be analyzed in the mass spectrometer in a similar manner. While the above-described "parking" approach and "peak-scanning" approach can be carried out separately, measurements made using parking and peak-scanning can be used in a single analysis.

The above-described analyzing, as well as that described below, can be carried out as described in the above referenced U.S. Provisional Application No. 61/652,095, filed on May 25, 2012, the entire contents of which are incorporated herein by reference. The analyzing can also utilize one or more databases of isotopic information. The databases can be generated using the methods and apparatus described herein, or they can be generated using numerical simulations. A person of skill in the art would recognize the type of isotopic information that should be included in a database to be used in the methods described herein. For example, such databases would include commonly observed proportions of fragment and adduct ions in the full mass spectrum of analytes of interest, as measured under common (or consistent) instrumental tuning conditions (including properties such as the electron impact energy of the ion source and source pressure of the analyte or compound being introduced into the mass spectrometer).

Standardization

All analyses described herein can be standardized by comparison with reference materials (e.g., reference analytes) having known (or preset) isotopic compositions, including predetermined (or preset) proportions (or concentrations) of isotopologues of interest. The reference materials can be analyzed under conditions (i.e., chemical purity, ion-source pressure and instrument settings) that are closely similar to those of the unknown samples (e.g., the analyte). Additionally, the reference materials can be converted to ions, separated and detected according the methods described above with respect to the analyte. The description provided below illustrates some means by which these standards can be created and characterized. As described below, analysis of the standards (e.g., reference materials) can be used to calibrate several instrumental artifacts.

For example, standardization can include alternate measurement of a sample (e.g., an analyte) and a standard (e.g., one or more reference materials) according to the methods described herein (e.g., converting the analyte or standard to ions, separating and detecting the ions as described above with respect to the analyte). In one embodiment, each of the analyte and the standard is drawn from a relatively large ($\sim 10^{-6}$ mol or larger) reservoir of gas (e.g., a gas containing the analyte or standard) and delivered to the ion source through a capillary bleed (e.g., one of the conduits 15-18 described with respect to FIG. 2) at a rate that varies little with time (e.g., as a continuous flow). For example, the standard can be drawn from the relatively large reservoir of gas by the sample introduction system and introduced into the ion source. The standard can then be converted to ions by the ion source and the ions can be separated by the entrance slit, the energy filter and the momentum filter. The separated ions of the standard can be detected by the detectors and then analyzed. The process can then be repeated for analyte drawn from another relatively large reservoir of gas that is different from the standard. The process can also then be repeated for another standard that is the same as or different from the first standard. Each time the gas stream entering the ion source (e.g., the ion source 30) is alternated from sample to standard or standard to sample, the operator can wait several seconds until ion intensities reach stable, relatively time-invariant values before recording signal intensities.

As with the analyte, reference materials delivered by the sample introduction system 20 as a continuous flow can be detected by either concurrently detecting the reference material ions using two or more detectors (e.g., the above-described concurrent detection 140a or "parking") or by scanning the reference material ion across at least one detector (e.g., the above-described concurrent detection 140b or "peak scanning").

When the reference material ions are concurrently detected by two or more detectors (e.g., the above-described concurrent detection 140a or "parking"), intensities detected (or registered) for two or more separate masses are recorded and averaged over a specified period of time (generally seconds) before switching the gas flow to another reservoir (e.g., from sample to standard or standard to sample). This process is repeated two or more times, generating a time series of observations of two or more ion intensities (and thus one or more intensity ratios) for sample (e.g., analyte) and standard (e.g., reference material). Interpolation between any two standard measurements provides the basis for standardizing the intervening sample measurement. Aspects of this method are based on techniques common to existing dual-inlet gas source isotope ratio mass spectrometers.

When the reference material ions are concurrently detected according to the "peak scanning" approach 140b, all reference ion beams having a single cardinal mass are scanned across at least one detector 82 (e.g., at least one collector). The reference ion beams can be scanned by adjusting the accelerating potential of the ion beams (e.g., by adjusting the accelerating potential of the ion source 30 or the energy filter 40) or by adjusting the magnetic field strength of the momentum filter 60 (e.g., by adjusting the intensity of a current delivered to an electromagnet included in the momentum filter).

As with the analyte, the "peak scanning" can be done using a single detector, or using two or more detectors as part of the same scan. This results in a time varying intensity at each detector, where variations in intensity reflect changing proportions of the various ion species that contribute to the population of ions at each cardinal mass, as shown in the mass spectrum of FIG. 7E. According to this embodiment, gas flow to the ion source should be relatively stable over the time scale of each scan (though subtle variations may be corrected for by introducing a modest correction to intensity as a function of time to account for depletion of a vapor reservoir being analyzed, or other similar artifacts). Resulting composite peaks can be de-convolved for the relative intensities of their component ion beams by methods readily understood by those of skill in the art, such as through an algorithm that assumes an initial guess as to the number, identity and relative intensities of the component ion beams and then iteratively solves for the least-squares best fit relative intensities of those ion beams.

For example, a program, such as a MATLAB® script (MATLAB is a registered trademark of The Mathworks Inc., Delaware USA), can be used to construct a synthetic data set by stipulating, for example, the shapes of the ion beams (e.g., the widths of the ion beams), the width of the detector, the intensity of a first ion beam, and the intensity of a second ion beam. The program can then produce a simulated mass spectrum based on the stipulated conditions and compare the simulated mass spectrum to the measured mass spectrum. The program can then iteratively solve for the least-squares best fit relative intensities of the ion beams (e.g., by searching for the set of conditions that best match the measured mass spectrum) to thereby determine the relative contribution of each ion beam to the measured mass spectrum. Standardization can be achieved by performing the above-described operations for a standard gas stream (e.g., analyte or reference material of the same chemical composition and source pressure as the sample but having a known or preset composition) near in time to the analysis of the sample (e.g., the analyte), and under closely or relatively similar source pressures and instrument settings to those used for the sample. The relative intensities of component ion beams determined for sample (e.g., analyte) and standard (e.g., reference material) are recorded and used in one or more of the standardization schemes described below.

In an alternative embodiment, a sample (e.g., an analyte) and a standard (e.g., a reference material) can be measured alternately, where each is, introduced to the ion source (e.g., the ion source 30) through time-resolved pulses contained within a helium carrier gas stream that continuously flows into the ion source or is added to the ion source through a separate capillary bleed concurrent with introduction of the helium carrier gas. According to this embodiment, the method includes concurrently detecting (e.g., concurrently detecting according to the "parking" 140a described above), for any one pulse of sample (standard or analyte), the ion intensity of molecular ions having two or more different masses for any one pulse of sample, standard or analyte, the masses of the molecular ions differing from one another by at least 1 AMU. The ion intensities are integrated over the duration of the pulse. Signals registered during periods of unstable or negligibly small signal intensities at the beginning and end of each pulse can be omitted to improve the quality of the data obtained. Standardization can be achieved by comparing ion intensity ratios measured for pulses of the analyte of the sample to those measured for pulses of the standard (e.g., the reference material) introduced before and/or after the sample analyte pulse, either by the averaging of all bracketing standard analyses or by interpolation between any two bracketing standard analyses. Aspects of this method are based on that common to existing carrier gas isotope ratio mass spectrometers.

Examples of several parameters (e.g., instrumental artifacts) that can be standardized are described in more detail below.

Instrumental Mass Bias

Figure 8:
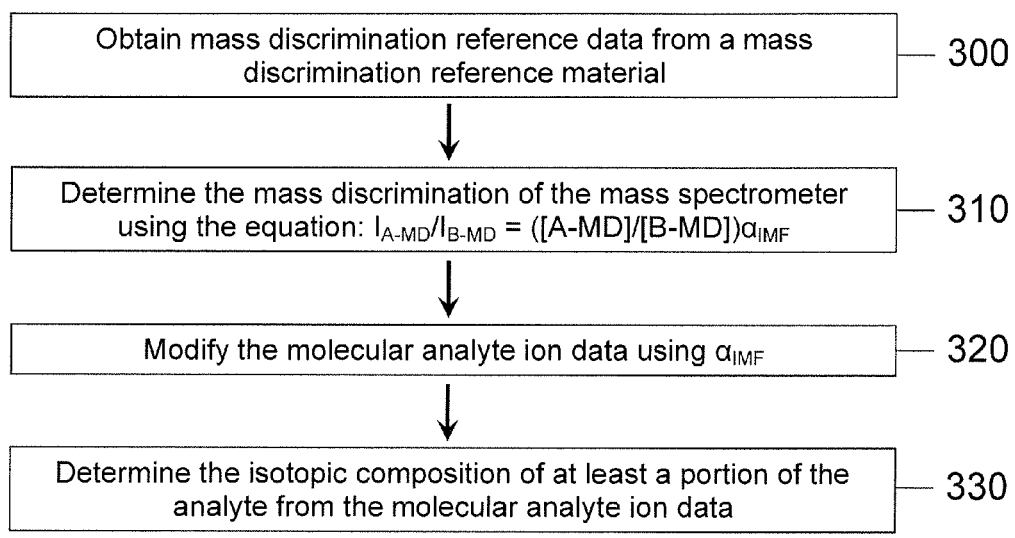
FIG. 8 is a flowchart showing a component of a method for determining the isotopic composition of an analyte in a sample according to an embodiment of the invention.

The mass discrimination in the above-described ion source 30, energy filter 40 and detector array 80 of the mass spectrometer 10 can be calibrated by comparing mass discrimination reference data (e.g., an ion intensity ($I_i$) ratio) for two or more mass discrimination reference ion beams to the known (or preset) concentrations of the isotopologues or isotopomers from which the mass discrimination reference ion beams are produced by electron impact ionization. For example, as shown in FIG. 8, calibrating the mass discrimination of the mass spectrometer can include (300) obtaining mass discrimination reference data from a mass discrimination reference material including mass discrimination reference isotopologues or isotopomers A-MD and B-MD that differ in their respective mass to charge ratios and have respective mass discrimination reference concentrations [A-MD] and [B-MD]. The mass discrimination reference data can be obtained by analyzing the mass discrimination reference material according to the methods described above with respect to the analyte. The mass discrimination reference data includes mass discrimination reference ion intensities $I_{A-MD}$ and $I_{B-MD}$ corresponding to the respective mass discrimination reference isotopologues or isotopomers A-MD and B-MD. The method according to this embodiment can further include (310) determining the mass discrimination of the mass spectrometer by comparing a ratio of the mass discrimination reference ion intensities $I_{A-MD}$ and $I_{B-MD}$ to a ratio of the mass discrimination reference concentrations [A-MD] and [B-MD] using a constant of proportionality $\alpha_{IMF}$ according to the Equation:

$$I_{A-MD}/I_{B-MD}=([A-MD]/[B-MD])\alpha_{IMF}$$

The molecular analyte ion data acquired according to the methods described above can then be modified using the constant of proportionality $\alpha_{IMF}$ (320). The isotopic composition of at least a portion of the analyte can then be determined from the modified molecular analyte ion data.

Instrument Linearity

Figure 9:
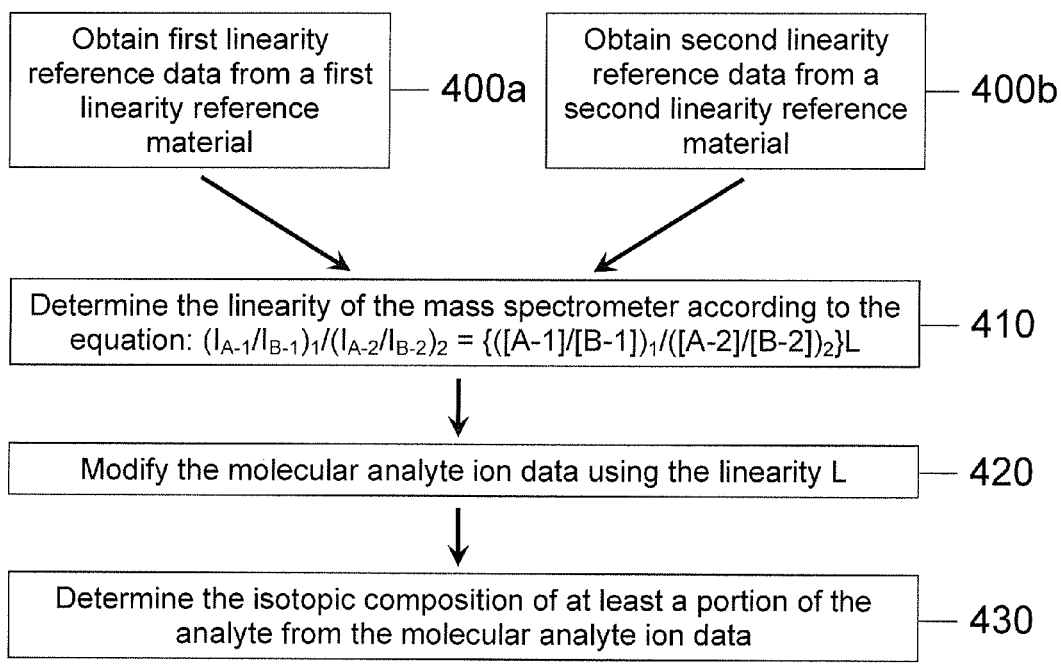
FIG. 9 is a flowchart showing a component of a method for determining the isotopic composition of an analyte in a sample according to an embodiment of the invention.

The instrument "linearity" (L) can be defined as a constant of proportionality between a measured ratio of reference ion intensity ratios for two reference materials (e.g., standards) to a ratio of abundance ratios of the relevant parent isotopologues or isotopomers. For example, as shown in FIG. 9, calibrating the linearity of the mass spectrometer 10 can include (400a) obtaining first linearity reference data from a first linearity reference material including first linearity reference isotopologues or isotopomers A-1 and B-1 at a first linearity reference concentration ratio $([A-1]/[B-1])_1$. The first linearity reference data can be obtained by analyzing the first linearity reference material according to the methods described above with respect to the analyte. The first linearity reference data includes a first linearity reference intensity ratio $(I_{A-1}/I_{B-1})_1$ corresponding to the first linearity reference isotopologues or isotopomers A-1 and B-1. The method further includes (400b) obtaining second linearity reference data from a second linearity reference material including second linearity reference isotopologues or isotopomers A-2 and B-2 at a second linearity reference concentration ratio $([A-2]/[B-2])_2$. The second linearity reference data can be obtained by analyzing the second linearity reference material according to the methods described above with respect to the analyte. The second linearity reference data includes a second linearity reference intensity ratio $(I_{A-2}/I_{B-2})_2$ corresponding to the second linearity reference isotopologues or isotopomers A-2 and B-2 (400b). The method further includes (410) determining the linearity (L) of the mass spectrometer according to the Equation:

$$(I_{A-1}/I_{B-1})_1/(I_{A-2}/I_{B-2})_2 = \{([A-1]/[B-1]_1/ [A-2]/[B-2])_2\}L$$

The method can further include modifying the molecular analyte ion data using the linearity L (420). The isotopic composition of at least a portion of the analyte can then be determined from the modified molecular analyte ion data (430). The linearity of the mass spectrometer is an empirically measured analytical artifact and is expected to be specific to each instrument, analytical condition (e.g., analyte type, source pressure and instrument tuning condition) and measured ratio of interest. Thus, it can be calibrated by comparison of two or more standards (e.g., reference materials) that differ by a known (or preset) amount in abundance ratios of isotopic species of interest.

Fragmentation Probability

Some embodiments of the invention include measurements of ions that are charged fragments of analyte molecules. As a result, it can be useful to calibrate a relationship between an ion intensity of a fragment of interest (e.g., a molecular analyte fragment ion intensity or $I_{FA}$) to an intensity of corresponding to an ion of the intact molecule from which it is derived (e.g., an intact molecular analyte ion intensity or $I_{A-molecular}$). This can be achieved by calibration of a constant of proportionality $K_{fragmentation}$ for the fragmentation reaction through analysis of the intensity ratio of the molecular analyte fragment ion to the intact molecular analyte ion. For example, the molecular analyte ions can include the intact molecular analyte ions and the molecular analyte fragment ions. Each of the molecular analyte ions are formed by ionizing an intact molecule of the analyte and each of the molecular analyte fragment ions are formed by dissociating one or more of the intact molecules of the analyte or the intact molecular analyte ions. Additionally, the molecular analyte ion data includes the molecular ion intensity $I_{A-molecular}$ corresponding to one or more of the intact molecular analyte ions. The molecular analyte ion data also includes the molecular analyte fragment ion intensity $I_{FA}$ corresponding to one or more of the molecular analyte fragment ions.

Figure 10:
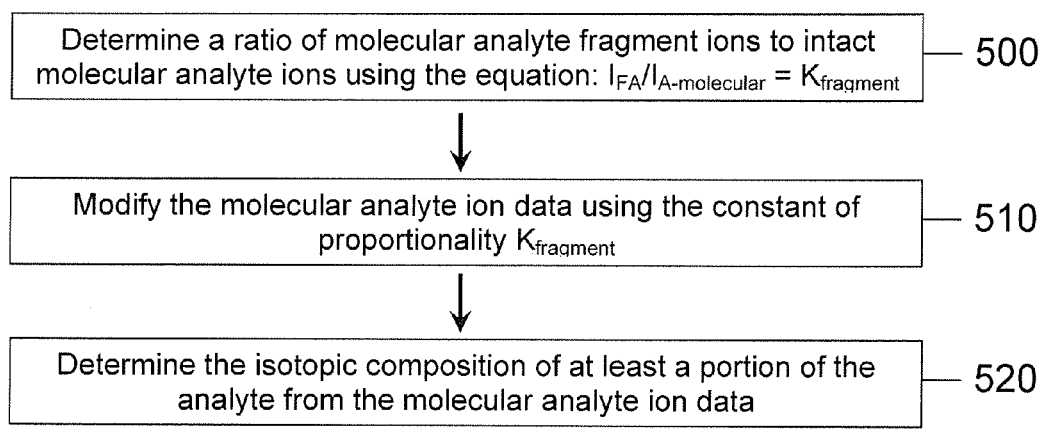
FIG. 10 is a flowchart showing a component of a method for determining the isotopic composition of an analyte in a sample according to an embodiment of the invention.

As shown in FIG. 10, embodiments of the invention include (500) determining a ratio of the molecular analyte fragment ions to the intact molecular analyte ions by calculating a constant of proportionality $K_{fragment}$ according to the Equation:

$$I_{FA}/I_{A-molecular} = K_{fragment}$$

The method also includes modifying the molecular analyte ion data using the constant of proportionality $K_{fragment}$ (510). The isotopic composition of at least a portion of the analyte can then be determined from the modified molecular analyte ion data (520). The constant of proportionality $K_{fragment}$ is an empirically measured analytical artifact, and is expected to be specific to each instrument, analytical condition (e.g., analyte type, source pressure and instrument tuning condition) and measured ratio of interest.

Adduct Probability

Some embodiments of the invention include measurements of ions that are ions or ionic fragments of the analyte molecules which have gained one or more excess H (or, potentially, other) atoms. As a result, it can be useful to calibrate a relationship between an ion intensity of adduct ions of interest (e.g., an analyte adduct ion intensity or $I_{A'-adduct}$) to an intensity corresponding to an ion of the un-adducted molecule from which it is derived (e.g., the molecular analyte ion intensity or $I_{A-molecular}$). This can be achieved by calibration of a constant of proportionality $K_{adduct}$ for the adduction reaction through analysis of the intensity ratio of the molecular analyte adduct ion to the intact molecular analyte ion. For example, the molecular analyte ions can include intact molecular analyte ions and analyte adduct ions. Each of the intact molecular analyte ions are formed by ionizing an intact molecule of the analyte and each of the molecular analyte adduct ions are formed by combining one or more of the intact molecules of the analyte or the analyte ions and a hydrogen atom or an other material, the other material being the same as or different from the analyte molecules or the analyte ions. Additionally, the molecular analyte ion data includes an intact molecular analyte ion intensity $I_{A-molecular}$ corresponding to one or more of the intact molecular analyte ions and a molecular analyte adduct ion intensity $I_{A'-adduct}$ corresponding to one or more of the molecular analyte adduct ions.

Figure 11:
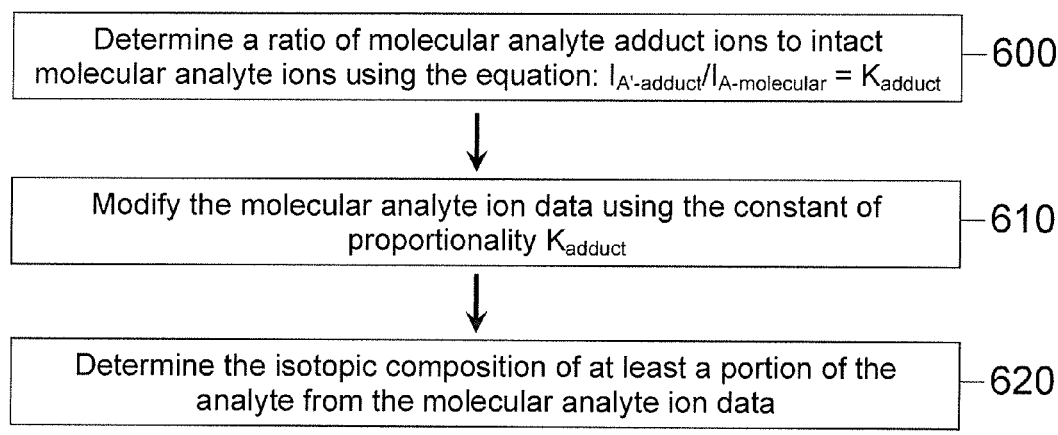
FIG. 11 is a flowchart showing a component of a method for determining the isotopic composition of an analyte in a sample according to an embodiment of the invention.

As shown in FIG. 11, embodiments of the invention include (600) determining a ratio of the molecular analyte adduct ions to the intact molecular analyte ions by calculating a constant of proportionality $K_{adduct}$ according to the Equation:

$$I_{A'-adduct}/I_{A-molecular} = K_{adduct}$$

The method further includes modifying the molecular analyte ion data using the constant of proportionality $K_{adduct}$ (610). The isotopic composition of at least a portion of the analyte can then be determined from the modified molecular analyte ion data (620). The constant of proportionality $K_{adduct}$ is an empirically measured analytical artifact, and is expected to be specific to each instrument, analytical condition (e.g., analyte type, source pressure and instrument tuning condition) and measured ratio of interest. The constant of proportionality $K_{adduct}$ is also expected to vary with the partial pressure of water in the ion source, and/or abundances in the ion source of other potential sources of H other than the analyte molecules.

Redistribution or Recombination Probability

Molecular ions can be generated by chains of electron-molecule, electron-ion, ion-ion and ion-molecule reactions that result in fragmentation of a parent species (e.g., an intact analyte molecule) and recombination of the resultant fragments to re-form ions that are indistinguishable in mass from the parent molecule (e.g., the intact analyte molecule or an ion thereof). Such reactions are sufficiently energetic that they effectively drive the sample (e.g., the analyte) toward a random distribution of isotopes among all possible isotopologues. Such effects, sometimes referred to as "scrambling," commonly result in redistribution of isotopes among isotopologues of approximately several percent, relative, of all measured molecular ions (e.g., molecular analyte ions). The foregoing effects can be standardized by comparison of two or more standards (e.g., reference materials) that differ by known (or preset) amounts in their isotopic distributions. In most instances, these effects cannot be standardized through analysis of a single ion beam intensity or ion intensity ratio; rather, one must monitor the change from expected values of the equilibrium constant for an isotope exchange reaction involving a homogeneous reaction among isotopologues of the same molecule.

Figure 12:
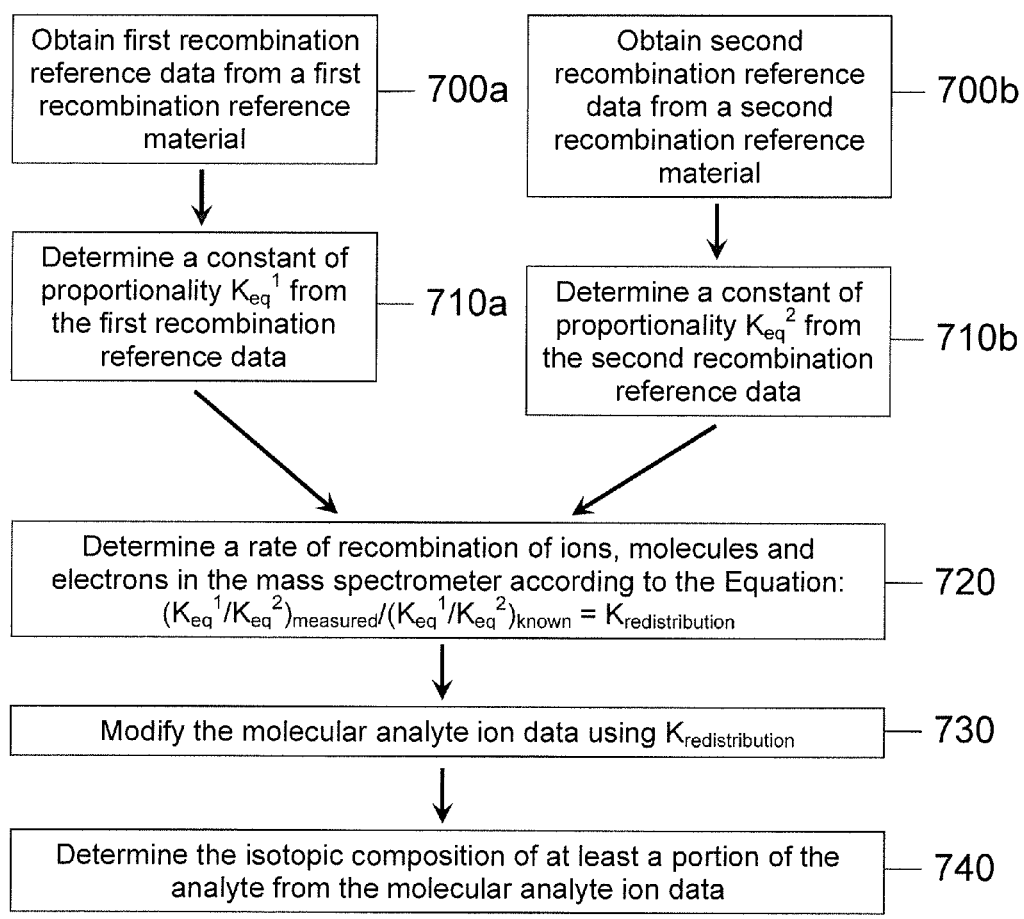
FIG. 12 is a flowchart showing a component of a method for determining the isotopic composition of an analyte in a sample according to an embodiment of the invention.

For example, as shown in FIG. 12, the method according to embodiments of the invention can include (700a) obtaining first recombination reference data from a first recombination reference material including first recombination reference isotopologues or isotopomers A-1 and B-1 and having a preset first recombination reference ratio of the first recombination reference isotopologues or isotopomers A-1 to the first recombination reference isotopologues or isotopomers B-1. The first recombination reference data can be obtained by analyzing the first recombination reference material according to the methods described above with respect to the analyte. The method also includes (710a) determining a constant of proportionality $K_{eq}^1$ from the first recombination reference data. The method further includes (700b) obtaining second recombination reference data from a second recombination reference material including second recombination reference isotopologues or isotopomers A-2 and B-2 and having a preset second recombination reference ratio of the second recombination reference isotopologues or isotopomers A-2 to the second recombination reference isotopologues or isotopomers B-2. The second recombination reference data can be obtained by analyzing the second recombination reference material according to the methods described above with respect to the analyte. The method also further includes (710b) determining a constant of proportionality $K_{eq}^2$ from the second recombination reference data, and (720) determining a rate of recombination of ions, molecules and electrons in the mass spectrometer according to the Equation:

$$(K_{eq}^1/K_{eq}^2)_{measured}/(K_{eq}^1/K_{eq}^2)_{known}=K_{redistribution}$$

The method also includes modifying the molecular analyte ion data using the constant of proportionality $K_{redistribution}$ (730). The isotopic composition of at least a portion of the analyte can then be determined from the modified molecular analyte ion data (740).

As an example of recombination and redistribution, $K_{eq}$ can be defined to be the equilibrium constant for the following reaction among methane isotopologues:

$$^{13}CH_4+^{12}CH_3D=^{13}CH_3D+^{12}CH_4$$

For example, $K_{eq}=[^{13}CH_3D][^{12}CH_4]/[^{13}CH_4][^{12}CH_3D]$, and $K_{eq}$ can be determined as the product of two isotopologue ratios (e.g., $[^{13}CH_3D]/[^{12}CH_3D]\times[^{12}CH_4]/[^{13}CH_4]$). As set forth above, a correction factor for redistribution through "scrambling" (e.g., $K_{redistribution}$) can be calculated through comparison of values of $K_{eq}$ for two known standards (e.g., reference materials), $K_{eq}^1$ and $K_{eq}^2$.

Migration Probability

Electron impact ionization is capable of driving migration of atoms between positions of an ion (e.g., an intact molecular analyte ion, an analyte fragment ion or a molecular analyte adduct ion). For example, the term "migration" can be used to describe the process by which a hydrogen atom in a methyl ($CH_3$) group of a propane molecule trades positions with a hydrogen atom in the $CH_2$ position of that same molecule. Such an effect can be standardized by comparison of two standards (or reference materials) that differ from one another by a known (or preset) amount in the concentrations of an isotope of interest in the two sites being investigated. For example, hydrogen isotope exchange between the two sites ('1' and '2') of a propane molecule through hydrogen migration can be calibrated according to the equation:

$$([D]_1/[D]_2)_{Measured}=([D]_1/[D]_2)_{Known}\times K_{migration}$$

Figure 13:
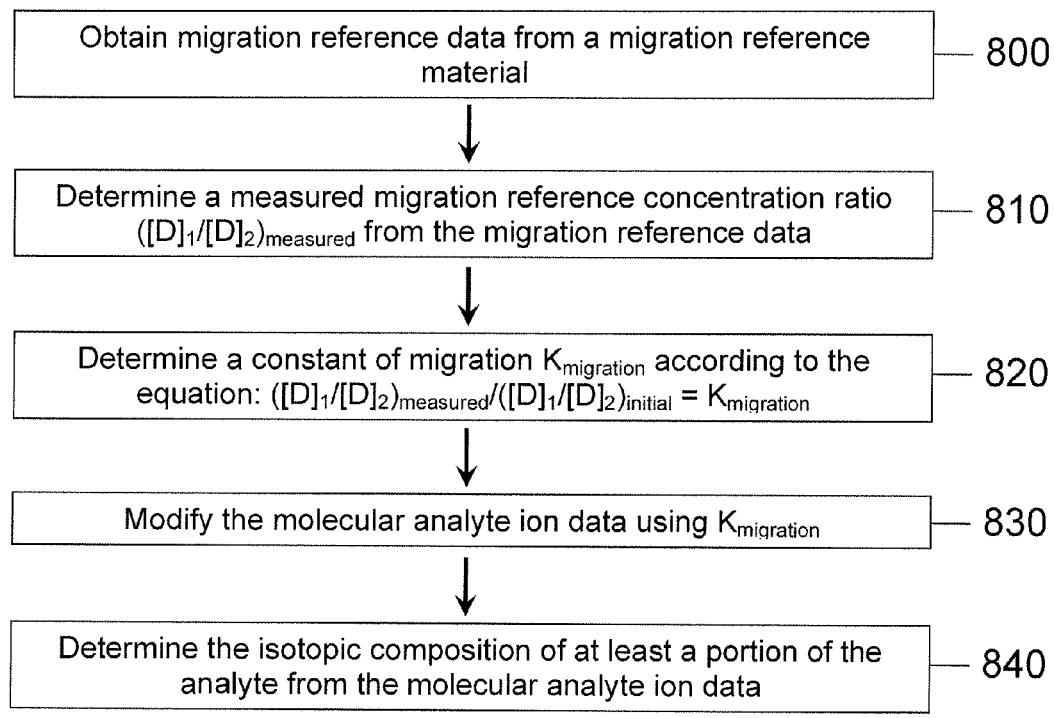
FIG. 13 is a flowchart showing a component of a method for determining the isotopic composition of an analyte in a sample according to an embodiment of the invention.

As shown in FIG. 13, according to embodiments of the invention the method can include (800) obtaining migration reference data from a migration reference material including isotopomers having an initial migration reference concentration ratio $([D]_1/[D]_2)_{initial}$. The migration reference data can be obtained by analyzing the migration reference material according to the methods described above with respect to the analyte. The method also includes (810) determining a measured migration reference concentration ratio $([D]_1/[D]_2)_{measured}$ from the migration reference data. The method further includes (820) determining a constant of migration $K_{migration}$ according to the Equation:

$$([D]_1/[D]_2)_{measured}/([D]_1/[D]_2)_{initial}=K_{migration}$$

The molecular analyte ion data can be modified using the constant of proportionality $K_{migration}$ (830). The isotopic composition of at least a portion of the analyte can then be determined from the modified molecular analyte ion data (840).

The above-described reference materials (e.g., the mass discrimination reference material, the first linearity reference material, the second linearity reference material, the first recombination reference material, the second recombination reference material, and the migration reference material) may each be any suitable material (e.g., any suitable compound) and they may each have a composition that is the same or different as that of the other reference materials or the analyte.

Standardization

In some embodiments, standardization of any or all of the above-described phenomena for unknown samples (e.g., unknown analytes) is independently or concurrently accomplished through "sample-standard bracketing," as described above, such as sequential analysis of a standard (e.g., a reference material), a sample of unknown composition, and a standard (e.g., another reference material that is the same as or different from the first reference material). For example, reference data can be first be obtained by analyzing a reference material according to the methods described above with respect to the analyte. Next analyte data can be obtained by analyzing an analyte data according to the methods described above. Then, additional reference data can be obtained by analyzing a reference material (which can be the same as or different from the reference material above) according to the methods described above with respect to the analyte. After the reference data, analyte data and additional reference data has been obtained, linear interpolation of the values measured for at least one or more of the constants $\alpha_{IMF}$, L, $K_{fragment}$, $K_{adduct}$, $K_{redistribute}$, or $K_{migration}$ (determined from the reference data and additional reference data according to the methods described above) for the bracketing standards to determine the values of the constants that should be applied to the unknown sample.

Figure 14:
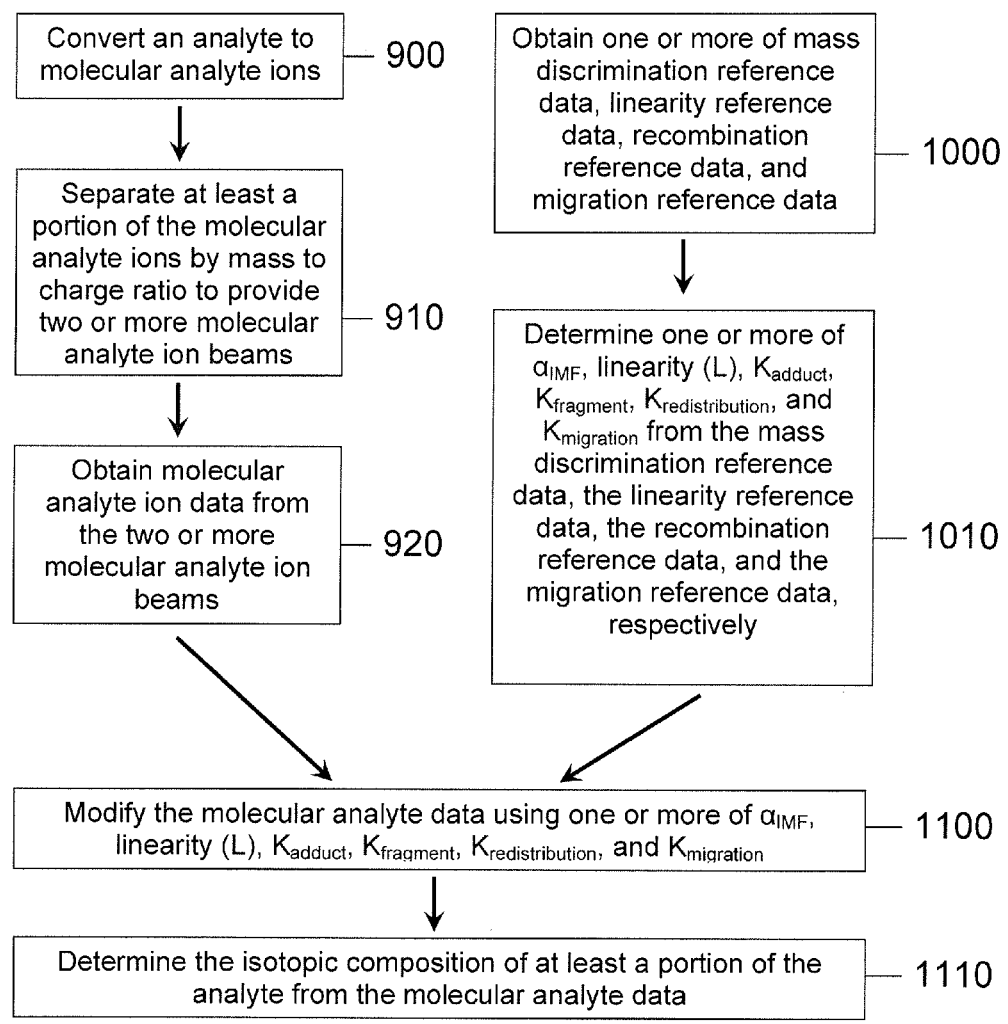
FIG. 14 is a flowchart showing a method for determining the isotopic composition of an analyte in a sample according to an embodiment of the invention.

For example, as shown in FIG. 14, the method according to embodiments of the invention can include (900) converting the analyte to molecular analyte ions using an ion source in a mass spectrometer. The method also includes (910) separating at least a portion of the molecular analyte ions by mass to charge ratio to provide two or more molecular analyte ion beams. The method further includes (920) obtaining molecular analyte ion data from the two or more molecular analyte ion beams. The molecular analyte ion data can be obtained according to the methods described above.

The method also further includes (1000) obtaining one or more of mass discrimination reference data, linearity reference data, recombination reference data, and migration reference data, and (1010) determining one or more of a linearity (L), a constant of proportionality $\alpha_{IMF}$, a constant of proportionality $K_{adduct}$, a constant of proportionality $K_{fragment}$, a constant of proportionality $K_{redistribution}$, and a constant of migration $K_{migration}$, which can be determined according to the methods described above. The method further includes modifying the molecular analyte ion data using one or more of $\alpha_{IMF}$, L, $K_{adduct}$, $K_{fragment}$, $K_{redistribution}$, and $K_{migration}$ (1100). The isotopic composition of at least a portion of the analyte can then be determined from the modified molecular analyte ion data (1110).

The number and frequency of the above-described bracketing measurements can vary with instrument conditions, analyte type and desired accuracy and precision. Based on prior experience with broadly similar instrumentation and measurements, $\alpha_{IMF}$ can be calibrated on time scales of tens of seconds (e.g., using the dual inlet changeover valve or multiple-injection carrier gas methods common to existing gas source isotope ratio mass spectrometers), values of $K_{fragment}$ and $K_{adduct}$ will be relatively constant over periods of hours to days, and values of L and $K_{redistribute}$ will be constant over periods of days to weeks. There is insufficient prior evidence to predict the variability of $K_{migration}$. The design purpose of having 4 gas reservoirs, each with its own capillary bleed, in the sample introduction system 20 (e.g., the inlet system) is to facilitate convenient comparison of an unknown sample (e.g., a sample including an analyte such as a gas or volatile organic compound introduced through a helium carrier gas) with multiple standards of known isotopic composition.

Statistical Determinations of Isotope Distributions

The methods described above are capable of determining the abundance ratios of isotopologues of molecular species and their derivatives (e.g., fragments thereof, adducts thereof, etc.). However, additional calculations can be used to establish positions of isotopes within these molecular species based on comparisons of respective isotopic compositions of a molecule and one or more of its fragments, or two or more of its fragments. This can be achieved through a combination of principles of sampling statistics with standardization of relevant analytical constants (e.g., $\alpha_{IMF}$, L, $K_{fragment}$, $K_{adduct}$, $K_{redistribute}$, $K_{migration}$), as described above.

For example, propane ($C_3H_8$) contains two non-equivalent carbon positions: a central ($CH_2$) position (hereafter, position 'A') and two symmetrically equivalent terminal methyl ($CH_3$) positions (hereafter position 'M'). The difference in $^{13}C$ concentration between these two positions can be determined by comparison of the abundance ratios: $[^{13}C^{12}C_2H_8]/[^{12}C_3H_8]$ and $[^{13}CH^{12}CH_5]/[^{12}C_2H_5]$, through simultaneous solution of the following family of equations (i.e., equations 1 through 4):

$$[^{13}C^{12}C_2H_8]/[^{12}C_3H_8] = (2[^{13}C]_M[^{12}C]_M[^{12}C]_A + [^{13}C]_A[^{12}C]_M^2)/([^{12}C]_M^2[^{12}C]_A]) \quad (1)$$

$$[^{13}C^{12}CH_5]/[^{12}C_2H_5] = ([^{13}C]_M[^{12}C]_A + [^{13}C]_A[^{12}C]_M)/([^{12}C]_M[^{12}C]_A]) \quad (2)$$

$$[^{13}C]_M + [^{12}C]_M = 1 \quad (3)$$

$$[^{13}C]_A + [^{12}C]_A = 1 \quad (4)$$

In equations 1 and 2, $[^{13}C]_M$, $[^{13}C]_A$, $[^{12}C]_M$ and $[^{12}C]_A$ refer to the $^{13}C$ and $^{12}C$ concentrations of the methyl (M) and alkyl (A) molecular sites.

Two additional expressions must hold true to account for the full isotopic inventory of both methyl and alkyl sites (i.e., $[^{13}C]_M$, $[^{13}C]_A$, $[12C]_M$, and $[^{12}C]_A$ must satisfy equations 3 and 4).

There are four unknowns ($[^{13}C]_M$, $[^{13}C]_A$, $[^{12}C]_M$ and $[^{12}C]_A$) in the above family of four equations. Thus, one can uniquely solve this family of equations, assuming that $[^{13}C^{12}C_2H_8]/[^{12}C_3H_8]$ and $[^{13}C^{12}CH_5]/[^{12}C_2H_5]$ have been correctly determined through mass spectrometric measurements of the relevant ion ratios (i.e., standardized to determine the relevant analytical constants) and assuming that the $C_2H_5$ fragment derives from the loss of one methyl group of the parent molecule (this last assumption is consistent with prior study of the fragmentation physics of propane, and can be verified on one embodiment of the mass spectrometer of the present invention through analyses of standards that have been highly enriched in $^{13}C$ in the central and terminal carbon positions). Thus, it is straightforward to convert two measurable ratios of molecular or fragment ions into fully constrained determinations of the proportions of $^{13}C$ contained in two structurally distinct molecular sites. Similar reasoning can be applied to a large number of other instances in which isotopic contents of positions in organic and other molecular structures can be reconstructed from the analysis of molecular and fragment ions.

Ion Correction of Non-Resolved Isobaric Interferences

Some molecular and fragment ion species may be difficult to resolve from nearby isobaric interferences, either due to the high total mass of the species in question or because the species is so low in abundance that it is preferable to perform mass spectrometric analysis with a large entrance slit and correspondingly high transmission but poor mass resolution. In such cases, abundances of unresolved species of interest may be determined by correction based on independent constraints on the proportions of all species contributing to a composite ion peak. $^{12}CH_3D$ methane serves as an illustrative example. The abundance of $^{12}CH_3D$ could be determined without direct mass resolved analysis if one measured the ion intensity ratio: $(I_{13CH4} + I_{12CH3D} + I_{12CH5})/I_{12CH4}$ and subtracted contributions from the two interfering species ($^{13}CH_4$ and $^{12}CH_5$) by separately measuring $^{13}CH_4/^{12}CH_4$ (a relatively easily measured ratio at moderate mass resolution) and $K_{adduct}$ (which can be determined through analyses of standard gases or reference materials, as described above).

EXAMPLES

Three examples of uses of the apparatus and methods according to embodiments of the invention follow. The examples are supported with data generated on a mass spectrometer according to one embodiment of the invention. The mass spectrometer used in the examples demonstrated a mass resolution (e.g., resolving power) up to 25,500 using the above described 5%-95% definition of mass resolution. Table 1 shows a comparison of the sensitivity and resolving power (e.g., mass resolution) of a mass spectrometer according to exemplary embodiments of the invention to a conventional MAT-253 mass spectrometer available from Thermo Fisher Scientific, Inc.

TABLE 1

|  | Entrance slit (μm) | Molecules/ ion | Resolving Power (5%/95%) |
| --- | --- | --- | --- |
| Conventional MAT-253 | 500 | 600 | ~500 |
| Example 1 | 250 | ~1,500 | 1,500-2,000 |
|  | 50 | ~7,500 | 7,500-10,000 |
|  | 25 | ~15,000 | 10,000-12,000 |
|  | 15 | ~20,000 | 12,000-15,000 |
|  | 5 | ~60,000 | 20,000-25,000 |

As can be seen in Table 1, the mass spectrometer according to embodiments of the invention exhibit significantly higher resolving power, but reduced sensitivity as compared to the conventional MAT-253 mass spectrometer available from Thermo Fisher Scientific, Inc. However, most stable isotope ratio measurements are made at ion currents >$10^9$ CPS and, therefore, the relatively lower sensitivity of embodiments of the invention is acceptable, as one can sacrifice a lot of signal and still obtain a precise measurement.

The mass spectrometer according to embodiments of the invention also demonstrated flat plateaus on hydrocarbon "ziggurat" peaks (e.g., peaks having the shape of a truncated pyramid, such as a pyramid having a flat top) as shown in the mass spectrum of FIG. 7E. The mass spectrometer according to embodiments of the invention has also demonstrated ~0.1‰ precision on faraday cup/electron multiplier ratio measurements. The mass spectrometer according to embodiments of the invention is noteworthy for its flexibility, mass range, ease of use for complex spectra, and it has significantly improved resolving power relative to ICP-MS instruments, which could be the result of: the stability of the Nier-type electron impact (EI) source, the narrow energy distribution of the source, and the improved vacuum in embodiments of the invention.

The apparatus and methods according to embodiments of the invention described herein can be used in various applications. For example, according to embodiments of the invention, a method of identifying a high-potential oil-field includes analyzing an analyte of a sample from a target field using an embodiment of the mass spectrometer and/or methods described herein to obtain relative proportions of isotopologues in one or more samples, such as methane, ethane or propane. The relative proportions of the isotopologues can be used to calculate equilibrium constants for isotope exchange reactions among the isotopologues (such as the reaction among methane isotopologues described below). Temperatures of gas formation or storage can be inferred by comparing these calculated equilibrium constants to the temperature-dependent values calibrated by theory or experiment. These temperatures can then be compared with known geothermal gradients to infer the depths in the earth of hydrocarbon generation and/or storage, which can then be used to guide drilling for oil and gas exploration.

Example 1

Methane Thermometry

As described above, the temperature of origin of methane or other hydrocarbons is useful for natural gas exploration and study of the environmental chemistry of methane. For example, the temperature of origin of methane constrains the depths and mechanisms of the source rocks from which the methane was obtained, and the temperature of storage informs exploration of the reservoirs where the methane is trapped. The temperatures of equilibration of molecules such as methane can be recorded by the proportions of their rare, heavy isotopes (e.g. $^{13}C$ and D) that form multiply substituted isotopologues (e.g., $^{13}CH_3D$) rather than singly substituted isotopologues (e.g., $^{13}CH_4$ and $^{12}CH_3D$). The proportions of the rare, heavy isotopes of methane are related through exchange reactions, such as:

$$^{12}CH_3D + ^{13}CH_4 = ^{13}CH_3D + ^{12}CH_4$$

The equilibrium constants for the exchange reactions of methane, such as the one shown above, are a function of temperature, and thus measurements of relative proportions of the four isotopologues involved in the reaction above provides a method of geochemical thermometry (e.g., a method of determining the temperature of origin and/or storage of a sample of methane). Such methods of thermometry have been previously determined for $CO_2$ and carbonate, and the principles of thermodynamics that explain this phenomenon are well known of $H_2$, $O_2$, $N_2$, CO, $N_2O$ and a variety of other simple molecular compounds. Similar principles apply to the isotopic abundances of multiply substituted isotopologues of ethane (e.g., $^{13}C_2H_6$) and higher order hydrocarbons.

Figure 15:
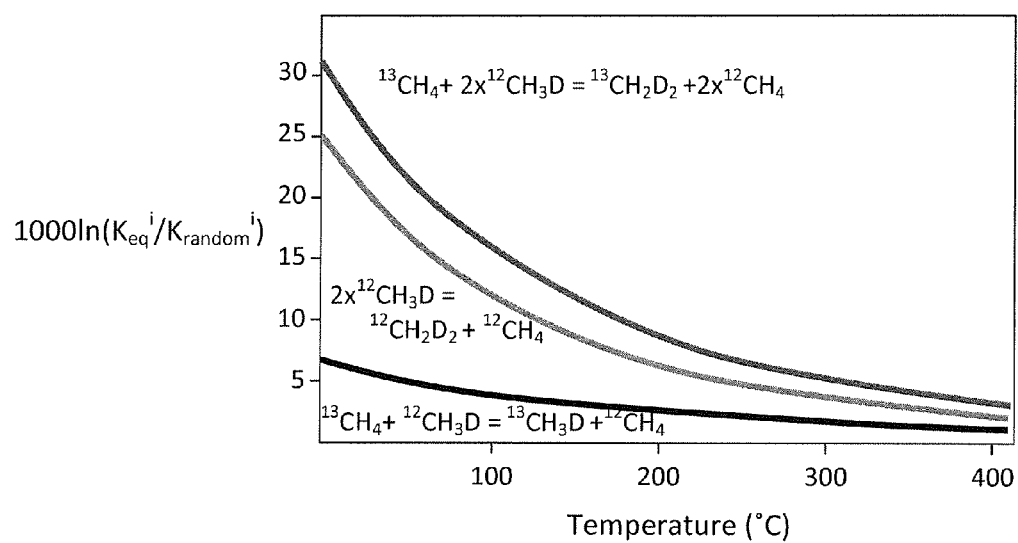
FIG. 15 is a graph illustrating predicted equilibrium constants for isotope exchange reactions involving homogeneous equilibria of methane isotopologues, including multiply substituted isotopologues.

The principles of statistical thermodynamics and the spectroscopy of methane indicate that the equilibrium constant for the above exchange reaction is ~1.005 at 300 K and decreases toward 1 roughly linearly with decreasing value of the quantity $(1/T^2)$, as shown in FIG. 15. FIG. 15 includes predicted equilibrium constants for isotope exchange reactions involving homogeneous equilibria of methane isotopologues, including multiply substituted isotopologues. The calculations were based on density functional theory predictions of the vibrational dynamics of methane and its isotopologues and quantum mechanical models of the relevant partition functions. Calculated equilibrium constants were normalized by the value for a random distribution of isotopes among all isotopologues and plotted as per mil (‰) deviations from that random distribution. A sufficiently precise and accurate measurement of the relative abundances of the four isotopologues of methane appearing in the above equation should permit one to determine the temperature of formation of methane. Similar principles lead to predictions regarding a large number of similar homogeneous isotope exchange equilibria among isotopologues of alkanes and other organic and inorganic molecules.

Table 2 below provides the precise masses and expected abundances of the four relevant isotopologues of methane for a sample equilibrated at 300 K and in which 1% of its carbon atoms are $^{13}C$ and 0.015% of its hydrogen atoms are D (i.e., approximately the natural isotopic abundances). The third and fourth columns of Table 2 list the expected (or predicted) ion currents, in both amps and counts per second, for all analyzed species at the detector, assuming an ion source with performance characteristics similar to commercial Nier-type electron impact sources (having typical ionization efficiencies), a gas pressure in the source similar to the operating conditions of common stable isotope ratio mass spectrometers (e.g., ~$10^{-7}$ mbar), and 1% transmission (e.g., a reduction in transmission of a factor of 100, corresponding to the transmission loss associated with use of the smallest source aperture to achieve high mass resolution). A usefully precise temperature estimate requires that the smallest of these ion intensities be measured with precision of ~0.01%.

TABLE 2

| Species | Mass (AMU) | Concentration | Ion current (amps) | Counts per second# |
|---|---|---|---|---|
| $^{12}CH_3D$ | 17.0376 | 5.94E−04 | 1.80E−12 | 1.13E+07 |
| $^{13}CH_4$ | 17.0347 | 9.99E−03 | 3.03E−11 | 1.89E+08 |
| $^{13}CH_3D$ | 18.0409 | 6.00E−06 | 1.82E−14 | 1.14E+05 |
| $^{12}CH_4$ | 16.0313 | 9.89E−01 | 3.00E−09 | 1.88E+10 |

Values in excess of $10^6$ are too high for anaylsis by electron multiplier; these ion beams are analyzed by faraday cup collection.

Figure 16A:
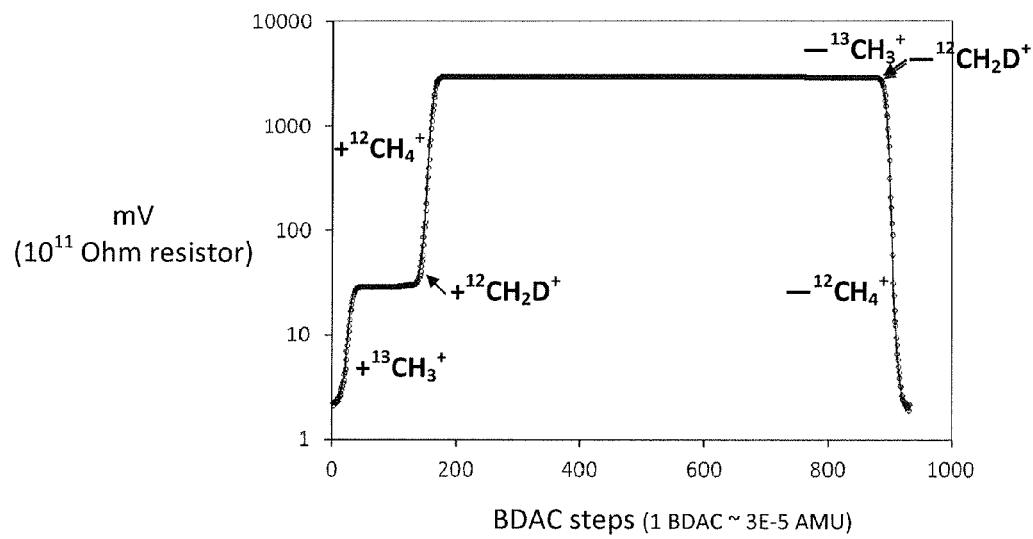
FIG. 16A is a graph illustrating the peak shape generated by scanning the mass 16 AMU analyte ion beam of methane across a single detector according to an embodiment of the invention.

As can be seen in FIG. 16A, which shows a mass spectrum (logarithmic scale) acquired for methane, the mass spectrometer according to an embodiment of the invention is capable of mass-resolving two representative isotopologues relevant to this measurement ($^{12}CH_4$ from the ion fragment, $^{13}CH_3$; it is not visually obvious, but both species are also discriminated from the minor beam of $^{12}CH_2D$ in this spectrum). The peak shape shown in FIG. 16A was generated by scanning the mass 16 AMU ion beam of methane across a single detector, using a mass spectrometer according to one embodiment of the invention. The locations at which the $^{13}CH_3^+$, $^{12}CH_2D^+$ and $^{12}CH_4^+$ ion beams enter and then exit the detector are shown in the mass spectrum of FIG. 16A.

Figure 16B:
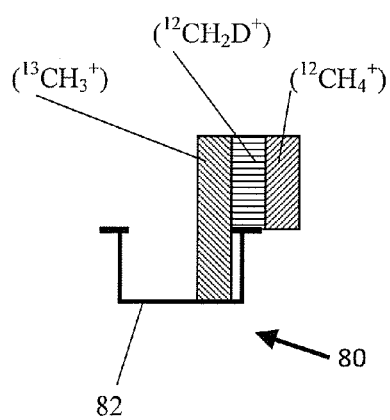
FIGS. 16B-G are partial schematic views showing three molecular ion beams derived from methane being scanned across a single detector.
Figure 16C:
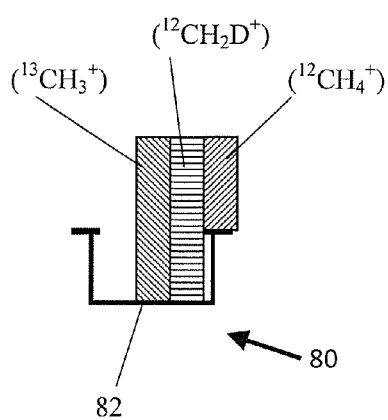
Figure 16D:
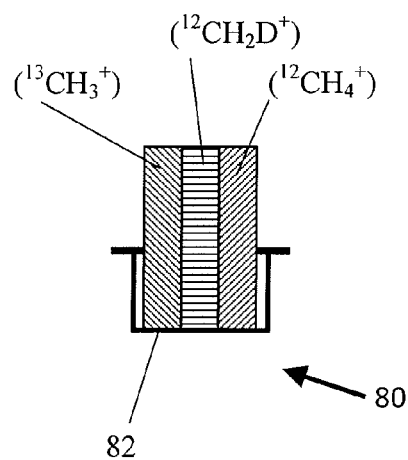
Figure 16E:
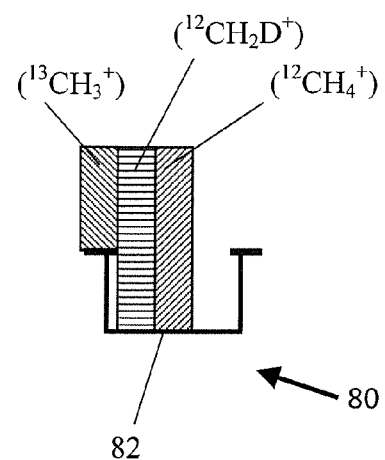
Figure 16F:
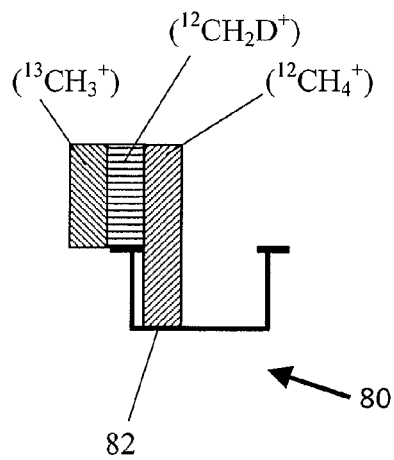
Figure 16G:
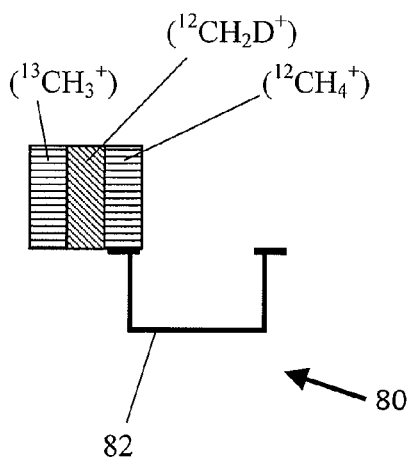

Additionally, FIGS. 16B-G show the $^{13}CH_3^+$, $^{12}CH_2D^+$ and $^{12}CH_4^+$ ion beams entering and then exiting a single detector 82 of a detector array 80. For example, FIG. 16B shows the $^{13}CH_3^+$ ion beam entering the detector. FIG. 16C shows the $^{12}CH_2D^+$ ion beam entering the detector such that both the $^{13}CH_3^+$ and $^{12}CH_2D^+$ ion beams are detected in the single detector concurrently (or simultaneously). Next, FIG. 16D shows the $^{12}CH_4^+$ ion beam entering the detector such that all three of the $^{13}CH_3^+$, $^{12}CH_2D^+$ and $^{12}CH_4^+$ ion beams are detected in the single detector concurrently (or simultaneously). FIG. 16E shows the $^{13}CH_3^+$ ion beam exiting the detector such that the $^{12}CH_2D^+$ and $^{12}CH_4^+$ ion beams are detected in the single detector concurrently (or simultaneously). FIG. 16F shows the $^{12}CH_2D^+$ ion beam exiting the detector such that only the $^{12}CH_4^+$ ion beam is detected in the detector. FIG. 16G shows the $^{12}CH_4^+$ ion beam exiting the detector.

The mass resolution of the peak scan shown in FIG. 16A is about 25,500 (using the 5%-95% definition described above). As can be seen in FIG. 16A, the mass spectrometer according one embodiment of the invention is capable of resolving $^{13}CH_3$ from $^{12}CH_4$. While it is not immediately clear in FIG. 16A, the minor ion beam $^{12}CH_2D$ is also well-resolved from $^{13}CH_3$ from $^{12}CH_4$. Similar performance is expected for diverse ions of methane, its fragments and adducts having other mass/charge ratios.

Figure 17:
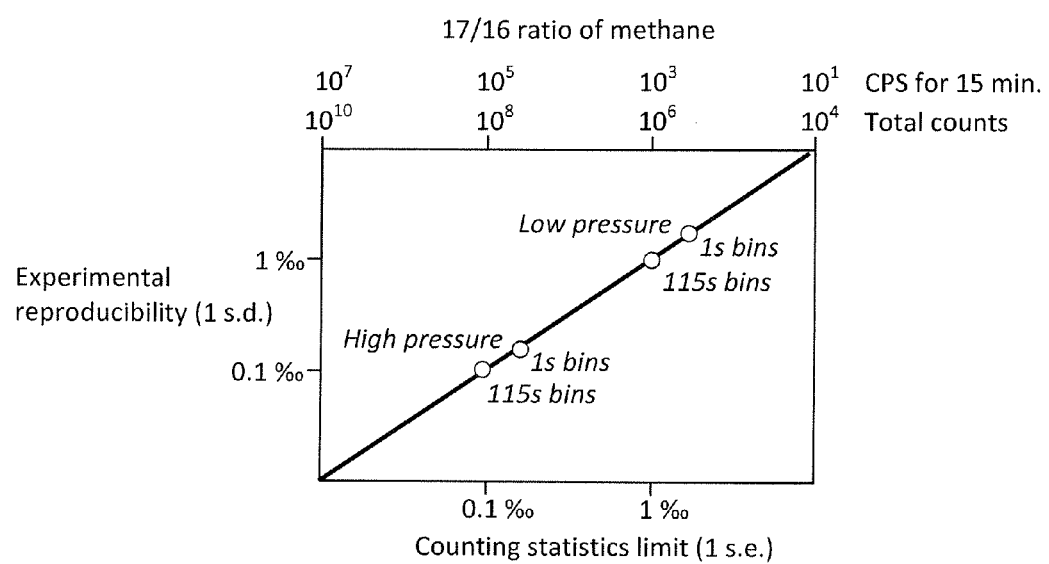
FIG. 17 is a graph illustrating the external precisions of replicate analyses of the mass 17/16 ratio of methane gas according to one embodiment of the invention.

FIG. 17 demonstrates the external precision that can be achieved through sample/standard bracketing in measurements of the ratio: $(^{13}CH_4+^{12}CH_3D+^{12}CH_5)/^{12}CH_4$ (i.e., the mass 17/16 ratio) for methane. These measurements were taken using a mass spectrometer according to one embodiment of the invention. Each point represents the standard deviation (1s) of measured ratios, where each measurement is the average over a 1 second or 115 second integration. Measurements were made at two different source pressures, to vary the counting rate. All measurements were made using electron multiplier detectors. The horizontal axis is the predicted standard error of each such measurement, based on counting statistics. As can be seen in FIG. 17, the above-described ratio was measured with external precision as good as 0.01 percent, relative, over a wide range of current integration times and signal intensities, indicating that the mass spectrometer according to an embodiment of the invention is capable of measuring ion intensity ratios with precision sufficient for the example applications described herein.

The mass resolutions and the precision of the above-described isotope ratio measurements are sufficient such that embodiments of the invention can be used to calibrate values of $\alpha_{IMF}$ and L for the two isotope ratios measured (e.g., $[^{13}CH_3D]/[^{12}CH_3D]$ and $[^{12}CH_4]/[^{13}CH_4]$) and for $K_{redistribution}$ for methane in the ion source. Three standards (e.g., reference materials) having distinct, known (or preset) isotopic compositions can be used to calibrate all three of these analytical constants prior to analysis of an unknown sample (e.g., a sample containing methane as an analyte having unknown isotopic composition). This standardization can be accomplished using embodiments of the invention through the repeated sequential analysis of three standards (e.g., reference materials) and one sample of unknown composition (e.g., an analyte having unknown isotopic composition), by alternately measuring the gas streams emanating from four flexible bellows of the inlet system of the mass spectrometer. $K_{fragmentation}$ and $K_{migration}$ are not relevant to any of the species analyzed for the above-described analysis of methane; if required to make measurements for analogous applications to molecules more complex than methane, $K_{fragmentation}$ and $K_{migration}$ can be calibrated through study of additional standards.

Measurements similar to those above may also be useful for carbon dioxide ($CO_2$), which has 18 naturally occurring isotopologues ($^{12}C^{16}O_2$, $^{12}C^{18}O_2$, $^{14}C^{18}O^{17}O$, etc.), each of which is unique in its physical and chemical properties and thus constitutes a potential independent tracer of source, reaction mechanism and/or environment of origin. Other methods of mass spectrometric or spectroscopic analysis of $CO_2$ isotopologues are capable of determining relative abundances of only 5 of these species ($^{12}C^{16}O_2$, $^{13}C^{16}O_2$, $^{14}C^{16}O_2$, $^{12}C^{18}O^{16}O$, and $^{12}C^{17}O^{16}O$). Any information encoded in the proportions of the other remaining 13 species is effectively lost by those other measurements.

Example 2

Position-Specific Isotope Composition of n-Alkanes

Another embodiment is directed to the determination of relative abundances of $^{13}C$-bearing isotopologues of the $CH_3^+$ and $C_2H_5^+$ ion fragments generated by ionization of propane. The foregoing data, combined with characterizations of the empirical constants describing fragmentation and recombination reactions in the ion source, can be used to determine the difference in $^{13}C$ content between the terminal and central carbon positions of propane. This difference is predicted to be a function of temperature in thermodynamically equilibrated propane (and thus can be used to establish the temperature of formation, as for the methane analysis described above). In non-equilibrated gases, this difference may illuminate the chemical kinetic mechanisms of natural gas maturation, and thus also aid in the exploration and development of oil and gas deposits.

Naturally occurring n-alkanes (e.g., methane, ethane, propane, etc.) are products of diverse processes, such as thermal degradation of organic matter, hydrothermal reactions of aqueous solutions, and biosynthesis; many are also products of industrial chemical synthesis. The carbon and hydrogen isotope content of the n-alkanes is a function of both the carbon sources from which they were synthesized and the conditions and chemical mechanisms of their synthesis. Thus, forensic identification and source attribution of organic molecules may be achieved based on the isotopic fingerprints of the organic molecules, including but not restricted to the carbon and hydrogen isotope compositions of n-alkanes. Measurements made with embodiments of the invention include several novel constraints to the isotopic fingerprint of alkanes and thereby facilitate determination of the sources of the alkanes. In embodiments of the invention, some of the novel measurements include: determination of the $^{13}C/^{12}C$ ratios of non-equivalent sites in alkane structures, determination of the D/H ratios of non-equivalent sites in alkane structures, determination of the abundance of $^{13}C-^{13}C$ bonds (i.e., $^{13}C$ substitutions in two adjacent sites of the same molecule), and determination of the abundance of $^{13}$C-D bonds in methyl groups from the terminal positions of chain alkane structures (i.e., $^{13}$C substitutions immediately adjacent to a D substitution for H in the same methyl group).

Determination of the $^{13}$C/$^{12}$C ratios of non-equivalent sites in alkane structures can be accomplished by determining the $^{13}$C/$^{12}$C ratios of intact molecular analyte ions and of analyte fragment ions, and combining these data using mathematical expressions such as those described above (e.g., statistical determinations of isotope distributions). This approach is applicable to n-alkanes containing 3 or more carbons (i.e., propane and higher order hydrocarbons), and generally requires determination of one independent carbon isotope ratio (i.e., the $^{13}$C/$^{12}$C ratio of one analyte molecule or molecular analyte fragment) per non-equivalent carbon site.

Determination of the D/H ratios of non-equivalent sites in alkane structures can be accomplished by determining the D/H ratios of intact molecular analyte ions and of analyte fragment ions, and combining these data using mathematical expressions similar to those described above (e.g., statistical determinations of isotope distributions). This approach is applicable to n-alkanes containing 3 or more carbons (i.e., propane and higher order hydrocarbons), and generally requires determination of one independent hydrogen isotope ratio (i.e., the D/H ratio of one analyte molecule or molecular analyte fragment) per non-equivalent carbon site. Such measurements likely will require calibration of $K_{migration}$ analytical constants for some compounds and analytical conditions.

Determination of the abundance of $^{13}$C—$^{13}$C bonds (i.e., $^{13}$C substitutions in two adjacent sites of the same molecule) can be accomplished through principles similar to those described above (e.g., statistical determinations of isotope distributions), but can be constrained by measurements of abundances of doubly-substituted molecular analyte ions (e.g., $^{13}$C$_2$$^{12}$CH$_8$ propane) and their analyte fragments (e.g., $^{13}$C$_2$H$_5$ derived from the fragmentation of propane). Such measurements are possible for any species containing two or more adjacent carbon atoms (i.e., ethane and larger n-alkanes).

Determination of the abundance of $^{13}$C—D bonds in methyl groups from the terminal positions of chain alkane structures (i.e., $^{13}$C substitutions immediately adjacent to a D substitution for H in the same methyl group) can be accomplished through analysis of the $^{13}$CH$_2$D/$^{12}$CH$_3$ ratio of analyte methyl fragment ions (a minor but common species generated by electron impact ionization of alkanes).

The largest molecular analyte or analyte fragment ion mass that can be subjected to these measurements will vary as a function of analytical conditions (e.g., source water pressure, total pressure and tuning conditions), the level of precision desired, the strategy employed in ion collection (e.g., multi-collection or peak scanning), and the method of data processing (e.g., ion correction of non-resolved isobaric interferences). In some instances, the isotopic composition of the full analyte molecule can be easily and precisely determined using previously existing methods, and additional constraints from measurements of analyte fragment ions can be added according to embodiments of the present invention. Table 3 shows anticipated signal strengths for multiply substituted alkanes for a modest source pressure and an entrance slit having a width of about 5 µm.

TABLE 3

| Isotopes | abundance | count rate | time to 0.3% |
| --- | --- | --- | --- |
| 1 × $^{13}$C | 6 · 10$^{-2}$ | 3 pA | 1 s |
| 2 × $^{13}$C | 4 · 10$^{-3}$ | 1 · 10$^6$ cps | 9 s |
| 3 × $^{13}$C | 2 · 10$^{-4}$ | 5 · 10$^4$ cps | 200 s |
| 1 × $^{13}$C; 1 × D | 1 · 10$^{-4}$ | 4 · 10$^4$ cps | 230 s |

Embodiments of the present invention provide an increased number of compositional dimensions that can be investigated, which provides the opportunity to dramatically improve the specificity of "finger printing." For example, conventional analysis of n-alkanes yields two isotope ratios: $^{13}$C/$^{12}$C and D/H. However, a comprehensive analysis according to embodiments of the present invention would yield: 10 ratios for methane, 128 ratios for ethane, 512 ratios for propane, ~4,000 ratios for n-butane, ~32,000 ratios for n-pentane, and ~10$^8$ ratios for n-octane.

Example 3

Isotopic Anatomy of Glucose

Yet another embodiment of the invention is directed to the analysis of the proportions of $^{13}$C, D and/or $^{18}$O bearing isotopologues of ion fragments generated by delivering volatile organic compounds, such as derivatized sugars, into the ion source. The foregoing data, combined with characterizations of the empirical constants describing fragmentation and recombination reactions in the ion source, will allow for the characterization of isotopic fingerprints associated with diverse sources of such compounds and thus aid in the forensic studies of diverse organic compounds (functionally, any species that can be derivatized to create a compound that can be delivered to the ion source through a heated gas chromatographic column).

For example, a method for the diagnosis or treatment of a disease includes analyzing an analyte of a sample from a patient using an embodiment of the mass spectrometer and/or methods described herein to obtain the isotopic composition of at least a portion of the analyte. The method also includes comparing the isotopic composition obtained for the analyte to a database of isotopic compositions. The correlation between the isotopic composition obtained for the analyte and the database of the isotopic compositions can be used to determine a disease diagnosis or disease treatment protocol.

In another embodiment of the invention, a method of analyzing a drug or drug metabolite includes analyzing the drug or drug metabolite in a sample using an embodiment of the mass spectrometer and/or methods described herein to obtain the isotopic composition of at least a portion of the drug or drug metabolite. The method further includes comparing the isotopic composition obtained for the drug or drug metabolite to a database of isotopic compositions. The correlation between the isotopic composition obtained for the drug or drug metabolite and the database of isotopic compositions can be used to determine a property of the drug or the drug metabolite and is useful in the forensic study of diverse organic compounds.

Metabolic consumption of glucose in living organisms is characterized by isotopic fractionation of the residual glucose pool (e.g., change in isotopic composition of blood glucose as a function of the fraction consumed). Though many of the details of this fractionation are unknown, the principles of chemical physics relevant to chemical separation of isotopes indicate these effects can differ significantly with the conditions of glucose consumption (e.g., temperature) and the mechanism of consumption, possibly including subtle variations in the structures of relevant enzymes and other reactive sites. Thus, characterization of the isotopic anatomy of glucose could serve as a diagnostic tool for characterizing the function of metabolic processes relevant to diabetes and possibly other diseases. Accordingly, aspects of embodiments of the invention are directed toward determining the isotopic signatures of metabolites, including but not limited to the carbon, oxygen and hydrogen isotope compositions of components of the glucose molecule. Similar principles apply to other examples of biomolecules that are subject to metabolic consumption.

Glucose and its derivatives can be transmitted through a gas chromatograph and thus are suitable analytes for embodiments of the present invention. Glucose itself has slow transport times through conventional gas chromatograph columns, suggesting that, in some embodiments, the analysis might be better made on a faster-moving glucose derivative (e.g., a glucose derivative that elutes from a gas chromatograph column faster than glucose). On the other hand, components added to glucose derivatives can contribute substantially to some portions of the mass spectrum, which can complicate interpretation of the isotopic measurements of glucose derivatives. Nonetheless, those of ordinary skill in the art can properly select glucose derivatives that provide suitable measurement characteristics. Regardless, both options (direct analysis of glucose or analysis of a glucose derivative) yield analyzable products on electron impact ionization and so are suitable for analysis according to embodiments of the present invention.

The fragmentation spectrum of glucose under electron impact ionization includes more than 75 analyzable peaks in a conventional, low-resolution mass spectrum; each of these peaks is the result of several analyte ion beams corresponding to species that have the same cardinal mass (e.g., $^{13}C$ and $^{12}CH$, at mass 13 AMU, etc.). Many of these composite peaks occur below mass 60 AMU, and thus should contain one or more component analyte ion beams that can be uniquely mass resolved by the mass spectrometric analyzer according to embodiments of the invention, assuming a mass resolution of 20,000 or more. Others of these ion beams may be more difficult to mass resolve, but are possibly analyzable using methods such as peak scanning and ion correction of non-resolved isobaric interferences, as described above.

Take for example, the analyte ion beams of the glucose mass spectrum including analyte ions having respective masses of 28, 29 and 30 AMU; the corresponding portions of the glucose mass spectrum include large contributions from CO and its hydrogen adducts (e.g., $^{12}C^{16}O$ at mass 28 AMU, $^{12}CO^{16}H$, $^{13}C^{16}O$ and $^{12}C^{17}O$ at 29 AMU, and $^{12}C^{16}OH_2$, $^{13}C^{16}OH$, $^{12}C^{16}OD$, $^{12}C^{18}O$, and $^{13}O^{17}O$ at mass 30). The hydrogen bearing species of CO are easily mass resolvable from the non-hydrogen bearing species, whereas isobaric interferences among the isotopologues of the CO molecule are not easily mass resolvable. Thus, in some embodiments, one can measure the ratios: $([^{13}C^{16}O]+ {}^{12}C^{17}O])/[^{12}C^{16}O]$ and $(^{12}C^{18}O+^{13}C^{17}O])/[^{12}C^{16}O]$, as all common terrestrial materials share a common relationship between $^{17}O/^{16}O(R^{17})$ and $^{18}O/^{16}O(R^{18})$: $(R^{17}_{sample}/R^{17}_{seawater})=(R^{18}_{sample}/R^{18}_{seawater})^{0.528}$.

Combination of the two measured ratios listed above (e.g., $([^{13}C^{16}O]+^{12}C^{17}O])/[^{12}C^{16}O]$ and $(^{12}C^{18}O+^{13}C^{17}O])/[^{12}C^{16}O])$ with constraints on $R^{17}$ and $R^{18}$ permits unique solution for the $^{13}C/^{12}C$ ratio and $^{18}O/^{16}O$ ratio of the CO fragment of glucose. This fragment is derived from the C=O double bond group at the terminal (C1) position of the glucose molecule. Possible contributions from fragments and recombination products of other carbon and oxygen positions in the molecule are possible; the proportions of these contributions can be determined through analysis of synthetic isotopically labeled standards (this is effectively a case where standardization can be achieved through constraints on both $K_{migration}$ and $K_{redistribution}$). This example illustrates two pieces of information (e.g., $^{13}C$ and $^{18}O$ content of CO) that can be obtained from one of the known fragment ion peaks of glucose, and illustrates just a small fraction of all of the analyzable species.

According to another embodiment of the invention, a method for determining a prior temperature of a sample includes analyzing an analyte of the sample using an embodiment of the mass spectrometer described herein to obtain molecular analyte ion data. The method further includes analyzing the molecular analyte ion data to obtain the isotopic composition of at least a portion of the analyte. For example, the method can include determining the isotopic composition of at least a portion of an analyte in the sample according to one of the methods described herein. The method also includes comparing the isotopic composition obtained for the analyte to a database of isotopic compositions. The method further includes determining the prior temperature of the sample based on the correlation between the isotopic composition obtained for the analyte and the database of isotopic compositions.

According to another embodiment of the invention, a method of determining an amount of an anthropogenic contribution to an atmospheric concentration of an atmospheric gas includes analyzing an analyte of a sample using an embodiment of the mass spectrometer described herein to obtain molecular analyte ion data. The method further includes analyzing the molecular analyte ion data to obtain the isotopic composition of at least a portion of the analyte. For example, the method can include determining the isotopic composition of at least a portion of an analyte in the sample according to one of the methods described herein. The method further includes comparing the isotopic composition obtained for the analyte to a database of isotopic compositions. The method also includes determining the amount of the anthropogenic contribution to the atmospheric concentration of the atmospheric gas based on the correlation between the isotopic composition obtained for the analyte and the database of the isotopic compositions. In some embodiments, the analyte is one or more of methane, carbon dioxide, sulfates, hydrocarbons, noble gases, and simple volatile molecular species such as $H_2$, $O_2$, $N_2$, NO, and $N_2O$.

While the present invention has been described in connection with certain exemplary embodiments, it is to be understood that the invention is not limited to the disclosed embodiments, but, on the contrary, is intended to cover various modifications and equivalent arrangements included within the spirit and scope of the appended claims, and equivalents thereof. Throughout the text and claims, use of the word "about" reflects the penumbra of variation associated with measurement, significant figures, and interchangeability, all as understood by a person having ordinary skill in the art to which this invention pertains. Additionally, throughout this disclosure and the accompanying claims, it is understood that even those ranges that may not use the term "about" to describe the high and low values are also implicitly modified by that term, unless otherwise specified.

What is claimed is:

1. A mass spectrometer comprising:
an entrance slit having a width, the slit configured to guide a first output of molecular analyte ions along a path, the molecular analyte ions of the first output having energy levels;
an energy filter positioned along the path downstream from the entrance slit and configured to receive the first output of molecular analyte ions, the energy filter having a first radius of curvature along the path, the energy filter configured to filter the molecular analyte ions of the first output according to their energy levels and produce a second output of molecular analyte ions;
a momentum filter positioned downstream from the energy filter and configured to receive the second output of molecular analyte ions, the momentum filter having a second radius of curvature along the path, the momentum filter configured to filter the molecular analyte ions of the second output according to their momenta and produce a third output of molecular analyte ions, the third output of molecular analyte ions comprising at least two ion beams; and
a detector array positioned downstream of the momentum filter and configured to receive the third output of molecular analyte ions and resolve and concurrently detect the at least two ion beams,
wherein the width and the first and second radii of curvature are selected to provide a mass resolution at the detector array of 20,000 or greater.

2. The mass spectrometer of claim 1, wherein respective molecular analyte ions of the at least two ion beams have respective masses that differ from one another by about 1 atomic mass unit, and
wherein the width, the first and second radii of curvature, and the detector array are configured to resolve and concurrently detect the at least two ion beams at the detector array and to distinguish between molecular analyte ions within each ion beam at one part in 20,000.

3. The mass spectrometer of claim 1, wherein the third output of molecular analyte ions comprises at least two molecular analyte ions, respective masses of the at least two molecular analyte ions being the same when rounded to the nearest whole number, the width and the first and second radii of curvature are configured to resolve the at least two molecular analyte ions at the detector array, and the detector array is configured to concurrently detect the at least two molecular analyte ions.

4. The mass spectrometer of claim 1, wherein the width is about 5 µm to about 250 µm, the first radius of curvature is about 20 cm to about 25 cm, and the second radius of curvature is about 20 cm to about 25 cm.

5. The mass spectrometer of claim 1, wherein the width is about 5 µm, the first radius of curvature is about 22 cm and the second radius of curvature is about 23 cm.

6. The mass spectrometer of claim 1, further comprising an ion source along the path upstream from the entrance slit and configured to provide an electron impact energy of about 5 eV to about 150 eV and to provide the first output of molecular analyte ions to the entrance slit.

7. The mass spectrometer of claim 6, wherein the ion source is configured to provide an electron impact energy of about 25 eV to about 150 eV.

8. The mass spectrometer of claim 1, further comprising an ion source along the path upstream from the entrance slit and capable of providing an electron impact energy of less than 50 eV and configured to provide the first output of molecular analyte ions to the entrance slit.

9. A method of identifying a potential oil-field, the method comprising:
analyzing an analyte of a sample from a target field using the mass spectrometer of claim 1 to obtain molecular analyte ion data;
analyzing the molecular analyte ion data to obtain the isotopic composition of at least a portion of the analyte to determine relative proportions of at least a portion of isotopologues in the sample; and
comparing the relative proportions of the isotopologues of the analyte to a database.

10. The method of claim 9, wherein the analyte is a hydrocarbon.

11. The method of claim 10, wherein the hydrocarbon is selected from the group consisting of methane, ethane, propane, butane, pentane and hexane.

12. A method of analyzing a drug or a drug metabolite, the method comprising:
analyzing a drug or drug metabolite in a sample using the mass spectrometer of claim 1 to convert the drug or drug metabolite to molecular analyte ions and to obtain molecular analyte ion data;
analyzing the molecular analyte ion data to obtain the isotopic composition of at least a portion of the drug or drug metabolite; and
comparing the isotopic composition obtained for the drug or drug metabolite to a database of isotopic compositions.

13. A method of determining an amount of an anthropogenic contribution to an atmospheric concentration of an atmospheric gas, the method comprising:
analyzing an analyte of a sample using the mass spectrometer of claim 1 to obtain molecular analyte ion data;
analyzing the molecular analyte ion data to obtain the isotopic composition of at least a portion of the analyte; and
comparing the isotopic composition obtained for the analyte to a database of isotopic compositions.

14. The method of claim 13, wherein the analyte is selected from the group consisting of methane, carbon dioxide, sulfates, hydrocarbons, noble gases, $H_2$, $O_2$, $N_2$, NO and $N_2O$.

15. The method of claim 13, further comprising determining a limit on anthropogenic emissions of the gas based on a correlation between the isotopic composition obtained for the analyte and the database of isotopic compositions.

16. A method for the diagnosis or treatment of a disease, the method comprising:
analyzing an analyte of a sample from a patient using the mass spectrometer of claim 1 to obtain molecular analyte ion data;
analyzing the molecular analyte ion data to obtain the isotopic composition of at least a portion of the analyte; and
comparing the isotopic composition obtained for the analyte to a database of isotopic compositions.

17. A method for determining a prior temperature of a sample, the method comprising:
analyzing an analyte of the sample using the mass spectrometer of claim 1 to obtain molecular analyte ion data;
analyzing the molecular analyte ion data to obtain the isotopic composition of at least a portion of the analyte; and
comparing the isotopic composition obtained for the analyte to a database of isotopic compositions.

18. The method of claim 17, wherein the prior temperature is a temperature at which the sample was formed.

* * * * *